(12) United States Patent
Setti

(10) Patent No.: US 8,013,186 B2
(45) Date of Patent: Sep. 6, 2011

(54) HALOALKYL CONTAINING COMPOUNDS AS CYSTEINE PROTEASE INHIBITORS

(75) Inventor: Eduardo L. Setti, San Mateo, CA (US)

(73) Assignee: Virobay, Inc., Menlo Park, CA (US)

( * ) Notice: Subject to any disclaimer, the term of this patent is extended or adjusted under 35 U.S.C. 154(b) by 478 days.

(21) Appl. No.: 11/791,928

(22) PCT Filed: Dec. 1, 2005

(86) PCT No.: PCT/US2005/043344
§ 371 (c)(1),
(2), (4) Date: Apr. 10, 2008

(87) PCT Pub. No.: WO2006/060494
PCT Pub. Date: Jun. 8, 2006

(65) Prior Publication Data
US 2009/0023781 A1   Jan. 22, 2009

Related U.S. Application Data

(60) Provisional application No. 60/632,018, filed on Dec. 1, 2004.

(51) Int. Cl.
*C07C 233/00* (2006.01)
*A01N 37/18* (2006.01)
(52) U.S. Cl. .......................................... 564/123; 514/617
(58) Field of Classification Search .................. 564/123; 514/617
See application file for complete search history.

(56) References Cited

OTHER PUBLICATIONS

Hcaplus 2003:737516, "Cathepsin cystein protease inhibitors and their therapeutic use", Bayly et. al., 2003.*

* cited by examiner

*Primary Examiner* — Janet L Andres
*Assistant Examiner* — Heidi Reese
(74) *Attorney, Agent, or Firm* — Kilpatrick Townsend & Stockton LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

20 Claims, No Drawings

HALOALKYL CONTAINING COMPOUNDS AS CYSTEINE PROTEASE INHIBITORS

This application claims the benefit of the filing date of U.S. Provisional Application Ser. No. 60/632,018 filed Dec. 1, 2004, which is incorporated by reference herein.

FIELD OF THE INVENTION

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

STATE OF THE ART

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as in several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. In addition, cathepsin S is implicated in: allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of this class of enzymes, in particular molecules that inhibit cathepsins B, K, L, F, and/or S, will therefore be useful as therapeutic agents.

SUMMARY OF THE INVENTION

In one aspect, this invention is directed to a compound of Formula (I):

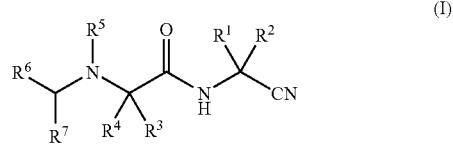

wherein:

$R^1$ is hydrogen, alkyl, haloalkyl, or alkoxyalkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) and $R^9$ is hydrogen, alkyl, haloalkyl, cycloalkyl, cycloalkylalkyl, aryl, aralkyl, heteroaryl, or heteroaralkyl wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monosubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl or halo or (ii) heterocyclylalkylene optionally substituted with one to four $R^c$ independently selected from alkyl or halo or optionally substituted with one to three $R^c$ where two $R^c$ are independently selected from alkyl, halo, haloalkyl, or hydroxyl and the third $R^c$ is hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^4$, -alkylene-$S(O)_{n2}$—$R^{15}$, —$COOR^6$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl;

$R^3$ is hydrogen or alkyl;

$R^4$ is alkyl, haloalkyl, cycloalkylalkyl, aralkyl, heteroaralkyl, heterocyclylalkyl, or -alkylene-$X^1$—$R^{22}$ [wherein $X^1$ is —$NR^{23}$, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CONR^{24}$—, or —$NR^{23}SO_2NR^{24}$— (where each $R^{23}$ and $R^{24}$ are independently hydrogen, alkyl, or acyl and n3 is 0-2) and $R^{22}$ is hydrogen, alkyl, haloalkyl, cycloalkyl, cycloalkylalkyl, aryl, aralkyl, heteroaryl, heteroaralkyl, heterocyclyl, or heterocyclylalkyl] wherein said alkylene chain in -alkylene-$X^1$—$R^{22}$ is optionally substituted with one to six halo and the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl; or $R^3$ and $R^4$ together with the carbon atom to which they are attached form cycloalkylene;

$R^5$ is hydrogen or alkyl;

$R^6$ is -haloalkylene-$X^2$—$R^{25}$ [wherein $X^2$ is single bond, —O—, or —$S(O)_{n4}$- where n4 is 0-2 and $R^{25}$ is alkyl, haloalkyl, cycloalkyl, cycloalkylalkyl, heterocyclyl, heterocyclylalkyl, aryl, aralkyl, heteroaryl, or heteroaralkyl] wherein the aromatic or alicyclic ring in $R^{25}$ is optionally substituted by one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl and further where the aromatic or alicyclic ring in $R^e$ is optionally substituted by one, two or three $R^f$ independently selected from alkyl, alkoxy, haloalkyl, haloalkoxy, halo, hydroxy, carboxy, cyano, nitro, aryl or cycloalkyl; and $R^7$ is alkyl, haloalkyl, aryl, heteroaryl, cycloalkyl, or heterocyclyl attached to the carbon atom substituted with the $R^7$ group via a carbon-carbon single bond; wherein the aromatic or alicyclic ring in $R^7$ is optionally substituted with one, two, or three $R^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl and further wherein the aromatic or alicyclic ring in $R^g$ is optionally substituted with one, two, or three $R^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl; or a pharmaceutically acceptable salts thereof.

In a second aspect, this invention is directed to a pharmaceutical composition comprising a compound of Formula (I) or a pharmaceutically acceptable salt thereof and a pharmaceutically acceptable excipient.

In a third aspect, this invention is directed to a method for treating a disease in an animal mediated by cysteine proteases, in particular cathepsin S, which method comprises administering to the animal a pharmaceutical composition comprising a therapeutically effective amount of a compound of Formula (I) or a pharmaceutically acceptable salt thereof and a pharmaceutically acceptable excipient.

In a fourth aspect, this invention is directed to processes for preparing compounds of Formula (I) and pharmaceutically acceptable salts thereof.

In a fifth aspect, this invention is directed to a method of treating a patient undergoing a therapy wherein the therapy causes an immune response, preferably a deleterious immune response, in the patient comprising administering to the patient a compound of Formula (I) or a pharmaceutically acceptable salt thereof. Preferably, the immune response is mediated by MHC class II molecules. The compound of this invention can be administered prior to, simultaneously, or after the therapy. Preferably, the therapy involves treatment with a biologic. Preferably, the therapy involves treatment with a small molecule.

Preferably, the biologic is a protein or an antibody, preferably a monoclonal antibody. More preferably, the biologic is Remicade®, Refacto®, Referon-A®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3.

Preferably, the treatment involves use of heparin, low molecular weight heparin, procainamide or hydralazine.

In a sixth aspect, this invention is directed to a method of treating immune response in an animal that is caused by administration of a biologic to the animal which method comprises administering to the animal in need of such treatment a therapeutically effective amount of a compound of Formula (I) or a pharmaceutically acceptable salt thereof.

In a seventh aspect, this invention is directed to a method of conducting a clinical trial for a biologic comprising administering to an individual participating in the clinical trial a compound of Formula (I) or a pharmaceutically acceptable salt thereof with the biologic.

In an eighth aspect, this invention is directed to a method of prophylactically treating a person undergoing treatment with a biologic with a compound of Formula (I) or a pharmaceutically acceptable salt thereof to treat the immune response caused by the biologic in the person.

In a ninth aspect, this invention is directed to a method of determining the loss in the efficacy of a biologic in an animal due to the immune response caused by the biologic comprising administering the biologic to the animal in the presence and absence of a compound of Formula (I) or a pharmaceutically acceptable salt thereof.

In a tenth aspect, this invention is directed to a method of improving efficacy of a biologic in an animal comprising administering the biologic to the animal with a compound of Formula (I) or a pharmaceutically acceptable salt thereof.

In an eleventh aspect, this invention is directed to the use of a compound of Formula (I) or a pharmaceutically acceptable salt thereof for the manufacture of a medicament. Preferably, the medicament is for use in the treatment of a disease mediated by Cathepsin S.

In a twelfth aspect, this invention is directed to the use of a compound of Formula (I) or a pharmaceutically acceptable salt thereof for the manufacture of a medicament for combination therapy with a biologic, wherein the compound of this invention treats the immune response caused by the biologic. Preferably, the compound(s) of the invention is administered prior to the administration of the biological agent. Preferably, the compound(s) of the invention is administered concomitantly with the biological agent. Preferably, the compound(s) of the invention is administered after the administration of the biological agent.

DETAILED DESCRIPTION OF THE INVENTION

Definitions

Unless otherwise stated, the following terms used in the specification and claims are defined for the purposes of this application and have the following meanings.

"Alicyclic" means cycloalkyl and heterocyclyl rings as defined herein.

"Alkyl" represented by itself means a straight or branched, saturated aliphatic radical containing one to six carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene (—$CH_2$—), ethylene (—$CH_2CH_2$—), trimethylene (—$CH_2CH_2CH_2$—), tetramethylene (—$CH_2CH_2CH_2CH_2$—) 2-methyltetramethylene (—$CH_2CH(CH_3)CH_2CH_2$—), pentamethylene (—$CH_2CH_2CH_2CH_2CH_2$—), and the like.

"Amino" means —$NH_2$ radical.

"Alkylamino" or "dialkylamino" refers to a —NHR and —NRR' radical respectively, where R and R' are independently alkyl group as defined above e.g., methylamino, dimethylamino, and the like.

"Alkoxy" refers to a —OR radical where R is an alkyl group as defined above e.g., methoxy, ethoxy, and the like.

"Alkoxycarbonyl" refers to a —C(O)OR radical where R is an alkyl group as defined above e.g., methoxycarbonyl, ethoxycarbonyl, and the like.

"Alkoxycarbonylalkyl" means an -(alkylene)-C(O)OR radical where R is alkyl as defined above e.g., methoxycarbonylmethyl, 2-, or 3-ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxy-ethyl, 1-, 2-, or 3-methoxypropyl, 2-ethoxyethyl, and the like.

"Alkoxyalkyloxyalkyl" refers to a -(alkylene)-O-(alkylene)-OR radical where R is an alkyl group as defined above, e.g., 2-methoxyethyloxymethyl, 3-methoxypropyloxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —$COR^a$ where $R^a$ is alkyl, and R' is hydrogen or alkyl as defined above e.g., aminomethyl, methylaminoethyl, dimethylaminoethyl, 1,3-diaminopropyl, acetylaminopropyl, and the like.

"Aminosulfonyl" refers to a —$SO_2R$ radical where R is —NRR' where R is hydrogen, alkyl, or —$COR^a$ where $R^a$ is alkyl, and R' is hydrogen or alkyl as defined above e.g., aminosulfonyl, methylaminosulfonyl, dimethylaminosulfonyl, and the like.

"Alkylthio" refers to a —SR radical where R is an alkyl group as defined above e.g., methylthio, ethylthio, and the like.

"Alkylsulfonyl" refers to a —$SO_2R$ radical where R is an alkyl group as defined above e.g., methylsulfonyl, ethylsulfonyl, and the like.

"Acyl" refers to a —COR radical where R is hydrogen, alkyl, haloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Aminocarbonyl" refers to a —CONRR' radical where R is hydrogen or alkyl and R' hydrogen, alkyl, aryl, aralkyl, heteroaryl, or heteroaralkyl.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are $sp^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aralkyl" refers to a -(alkylene)-R radical where R is aryl as defined above e.g., benzyl, phenethyl, and the like.

"Aryloxy" refers to a —OR radical where R is aryl as defined above e.g., phenoxy, and the like.

"Aryloxyalkyl" refers to a -(alkylene)-OR radical where R is aryl as defined above e.g., phenoxymethyl, 2-, or 3-phenoxymethyl, and the like "Arylsulfonyl" refers to a —$SO_2R$ radical where R is an aryl group as defined above e.g., phenylsulfonyl, and the like.

"Biologic" means a therapeutic agent originally derived from living organisms for the treatment or management of a disease. Examples include, but are not limited to, proteins (recombinant and plasma derived), monoclonal or polyclonal, humanized or murine antibodies, toxins, hormones, and the like. Biologics are currently available for the treatment of a variety of diseases such as cancer, rheumatoid arthritis, and haemophilia.

"Carboxy" refers to —C(O)OH radical.

"Carboxyalkyl" refers to a -(alkylene)-C(O)OH radical e.g., carboxymethyl, carboxyethyl, and the like.

"Cycloalkyl" refers to a monovalent saturated or partially unsaturated, monocyclic ring containing three to eight ring carbon atoms e.g., cyclopropyl, cyclobutyl, cyclopentyl, cyclohexyl, cyclohexenyl, 2,5-cyclohexadienyl, and the like.

"Cycloalkyloxy" refers to a radical —O—R where R is cycloalkyl group as defined above, e.g cyclopropyloxy, cyclohexyloxy, cyclopentyloxy, and the like.

"Cycloalkylalkyl" refers to a -(alkylene)-R radical where R is cycloalkyl as defined above e.g., cyclopropylmethyl, cyclobutylethyl, cyclobutylmethyl, and the like "Cycloalkylene" refers to a divalent saturated or partially unsaturated monocyclic ring containing three to eight ring carbon atoms. For example, the instance wherein "$R^1$ and $R^2$ together with the carbon atom to which both $R^1$ and $R^2$ are attached form cycloalkylene" includes, but is not limited to, the following:

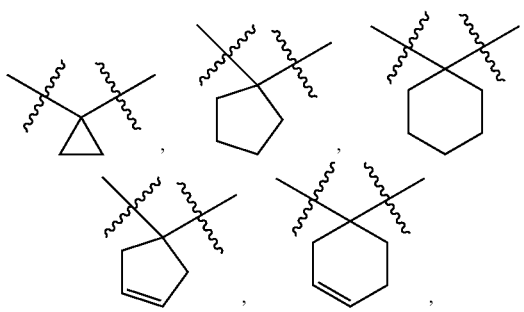

and the like.

"Disubstituted amino" refers to a —NRR' radical where R is alkyl, aryl, aralkyl, heteroaryl, heteroaralkyl, or heterocyclyl and R' is alkyl, aryl, aralkyl, heteroaryl, heteroaralkyl, cycloalkyl, heterocyclyl, cycloalkylalkyl, hydroxyalkyl, alkoxyalkyl, or acyl as defined herein. Representative examples include, but are not limited to, dimethylamino, methylphenylamino, benzylmethylamino, acetylmethylamino, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Deleterious immune response" means an immune response that prevents effective treatment of a patient or causes disease in a patient. As an example, dosing a patient with a murine antibody either as a therapy or a diagnostic agent causes the production of human antimouse antibodies that prevent or interfere with subsequent treatments. The incidence of antibody formation versus pure murine monoclonals can exceed 70%. (see Khazaeli, M. B. et al. *J. Immunother.* 1994, 15, pp 42-52; Dillman R. O. et al. *Cancer Biother.* 1994, 9, pp 17-28; and Reinsberg, *J. Hybridoma.* 1995, 14, pp 205-208). Additional examples of known agents that suffer from deleterious immune responses are blood-clotting factors such as factor VIII. When administered to hemophilia A patients, factor VIII restores the ability of the blood to clot. Although factor VIII is a human protein, it still elicits an immune response in hemophiliacs as endogenous factor VIII is not present in their blood and thus it appears as a foreign antigen to the immune system. Approximately 29-33% of new patients will produce antibodies that bind and neutralize the therapeutically administered factor VIII (see Lusher J. M. *Semin Thrombi Hemost.* 2002, 28(3), pp 273-276). These neutralizing antibodies require the administration of larger amounts of factor VIII in order to maintain normal blood clotting parameters; an expensive regimen of treatment in order to induce immune tolerance (see Briet E et al. *Adv. Exp. Med. Bio.* 2001, 489, pp 89-97). Another immunogenic example is adenoviral vectors. Retroviral therapy remains experimental and is of limited utility. One reason is that the application of a therapeutic virus generates an immune response capable of blocking any subsequent administration of the same or similar virus (see Yiping Yang et al. *J. of Virology.* 1995, 69, pp 2004-2015). This ensures that retroviral therapies must be based on the transient expression of a protein or the direct incorporation of viral sequence into the host genome. Directed research has identified multiple viral neutralizing epitopes recognized by host antibodies (see Hanne, Gahery-Segard et al. *J. of Virology* 1998. 72, pp 2388-2397) suggesting that viral modifications will not be sufficient to overcome this obstacle. This invention will enable a process whereby an adenoviral therapy will have utility for repeated application. Another example of an immunogenic agent that elicits neutralizing antibodies is the well-known cosmetic agent Botox. Botulin toxin protein, is purified from the fermentation of *Clostridium botulinum*. As a therapeutic agent, it is used for muscle disorders such as cervical dystonia in addition to cosmetic application. After repeated exposure patients generate neutralizing antibodies to the toxin that results in reduced efficacy (see Birklein F. et al. *Ann Neurol.* 2002, 52, pp 68-73 and Rollnik, J. D. et al. *Neurol. Clin. Neurophysiol.* 2001, 2001(3), pp 2-4). A "deleterious immune response" also encompasses diseases caused by therapeutic agents. A specific example of this is the immune response to therapy with recombinant human erythropoietin (EPO). Erythropoietin is used to stimulate the growth or red cells and restore red blood cell counts in patients who have undergone chemotherapy or dialysis. A small percentage of patients develop antibodies to EPO and subsequently are unresponsive to both therapeutically administered EPO and their own endogenous EPO (see Casadevall, N. et al., *NEJM.* 2002, 346, pp 469-475). They contract a disorder, pure red cell aplasia, in which red blood cell production is severely diminished (see Gershon S. K. et. al. *NEJM.* 2002, 346, pp 1584-1586). This complication of EPO therapy is lethal if untreated. Another specific example is the murine antibody, OKT3 (a.k.a., Orthoclone) a monoclonal antibody directed towards CD-3 domain of activated T-cells. In clinical trials 20-40% of patients administered OKT3 produce antibodies versus the therapy. These antibodies besides neutralizing the therapy also stimulate a strong host immune reaction. The immune reaction is severe enough that patients with high titers of human anti-mouse antibodies are specifically restricted from taking the drug (see Orthoclone package label). A final example is a human antibody therapeutic. Humira® is a monoclonal antibody directed against TNF and is used to treat rheumatoid arthritis patients. When taken alone ~12% of patients develop neutralizing antibodies. In addition, a small percentage of patients given the drug also contract a systemic lupus erthematosus-like condition that is an IgG-mediated immune response induced by the therapeutic agent (see Humira package label).

Another example of "deleterious immune response" is a host reaction to small molecule drugs. It is known to those skilled in the art that certain chemical structures will conjugate with host proteins to stimulate immune recognition (see Ju. C. et al. 2002. *Current Drug Metabolism* 3, pp 367-377 and Kimber I. et al. 2002, *Toxicologic Pathology* 30, pp 54-58.) A substantial portion of this host reactions are IgG mediated. Specific "deleterious immune responses" that are IgG mediated and include: hemolytic anemia, Steven-Johnson syndrome and drug induced Lupus.

"Halo" refers to fluoro, chloro, bromo or iodo.

"Haloalkyl" refers to alkyl as defined above substituted by one or more, preferably one to five, "halo" atoms, as such terms are defined in this application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkylene" refers to alkylene radical as defined above where one to six hydrogen atoms are replaced by chlorine or fluorine atoms(s), preferably one or two hydrogens are replaced with fluorine or chlorine atoms, more preferably two atoms on the same carbon of the alkylene chain are replaced with fluorine atoms e.g. dichloromethylene, difluoromethylene, 1,2-difluoroethylene, and the like.

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or multicyclic moiety of 5 to 10 ring atoms in which one or more, preferably one, two, or three, of the ring atom(s) is (are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothienyl, benzimidazolyl, quinolinyl, isoquinolinyl, quinazolinyl, quinoxalinyl, pyrazolyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaryloxyalkyl" refers to a -(alkylene)-OR radical where R is heteroaryl as defined above e.g., furanyloxymethyl, 2-, or 3-indolyloxyethyl, and the like.

"Heteroaryloxy" refers to a —OR radical where R is heteroaryl as defined above.

"Heteroaralkyloxy" refers to a —OR radical where R is heteroaralkyl as defined above.

"Heteroarylsulfonyl" refers to a —SO$_2$R radical where R is an heteroaryl group as defined above e.g., pyridinylsulfonyl, and the like.

"Heterocyclyl" refers to a saturated or partially unsaturated, mono or bicyclic radical of 4, 5 or 6 carbon ring atoms wherein one or more, preferably one, two, or three of the ring carbon atoms are replaced by a heteroatom selected from —N=, —N—, —O—, —S—, —SO—, or —S(O)$_2$— and further wherein one or two ring atoms are optionally replaced by a keto (—CO—) group. The heterocyclyl ring is optionally fused to aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, quinuclidinyl, and the like.

"Heterocyclylalkyl" refers to a -(alkylene)-heterocyclyl radical as defined in this Application. Representative examples include, but are not limited to, imidazolidin-1-yl-methyl, morpholin-4-ylmethyl, thiomorpholin-4-ylmethyl, thiomorpholin-4-ylmethyl-1-oxide, indolinylethyl, piperazinylmethyl or ethyl, piperidylmethyl or ethyl, pyrrolidinylmethyl or ethyl, and the like.

"Heterocyclyloxy" refers to a —OR radical where R is heterocyclyl as defined above e.g., piperidinyloxy, tetrahydrofuranyloxy, and the like.

"Heterocyclylsulfonyl" refers to a —SO$_2$R radical where R is an heterocyclyl group as defined above e.g., piperidinylsulfonyl, piperazinylsulfonyl, and the like.

"Heterocyclylalkylene" refers to a divalent heterocyclyl group, as defined in this application, e.g., the instance wherein R$^1$ and R$^2$ together with the carbon atom to which both R$^1$ and R$^2$ are attached form heterocyclylalkylene" includes, but is not limited to, the following:

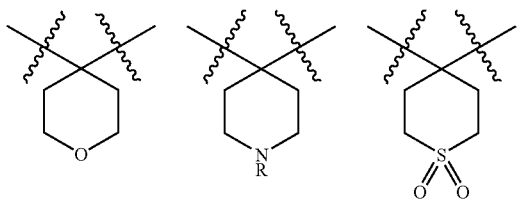

in which R is a substituent defined in the Summary of the Invention

"Hydroxy" means —OH radical.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this application to describe compounds of Formula (I) are meant to be encompassed all possible stereoisomers.

"Keto or oxo" means (=O) radical.

"Monosubstituted amino" refers to a —NHR radical where R is alkyl, aryl, aralkyl, heteroaryl, heteroaralkyl, cycloalkyl, cycloalkylalkyl, hydroxyalkyl, alkoxyalkyl, or acyl as defined herein. Representative examples include, but are not limited to, methylamino, phenylamino, benzylamino, cycloalkylmethylamino, acetylamino, trifluoroacetyl, and the like.

"Nitro" means —NO$_2$ radical.

"Optional" or "optionally" or "may be" means that the subsequently described event or circumstance may or may not occur, and that the description includes instances where the event or circumstance occurs and instances in which it does not. For example, the phrase "wherein the aromatic ring in R$^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)

benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999.

The expression "... wherein the aromatic or alicyclic ring in $R^2$, $R^4$, or $R^6$ is optionally substituted with one to three $R^a$, $R^d$, or $R^e$, respectively..." as used in the Claims refers to all the groups attached to $R^2$, $R^4$, and $R^6$ that contain an aromatic or alicyclic ring being optionally substituted with one to three $R^a$, $R^d$, and $R^e$ respectively. The aromatic or alicyclic ring may be directly attached to $R^2$, $R^4$, and $R^6$ or be part of a group that is directly attached to $R^2$, $R^4$, or $R^6$. For example, for $R^4$ it includes rings in cycloalkylalkyl, aralkyl, heteroaralkyl, heterocyclylalkyl, or -alkylene-$X^1$—$R^{22}$ [wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$, —$NR^{23}COO$—, —$OCONR^{23}$—, —$NR^{23}CONR^{24}$—, or —$NR^{23}SO_2NR^{24}$— (where each $R^{23}$ and $R^{24}$ are independently hydrogen, alkyl, or acyl and n3 is 0-2) and $R^{22}$ is cycloalkyl, cycloalkylalkyl, aryl, aralkyl, heteroaryl, heteroaralkyl, heterocyclyl, or heterocyclylalkyl] groups being optionally substituted with $R^d$.

The expression "... alkylene chain in -alkylene-$X^1$—$R^{22}$ is optionally substituted with one to six halo... as used in the Claims refers to the alkylene chain attached on either side of the $X^1$ group being optionally substituted with halo. The alkylene chain is present on the right side of $X^1$ when $R^{22}$ is cycloalkylalkyl, aralkyl, heteroaralkyl, or heterocyclylalkyl.

"Therapeutically effective amount" means that amount which, when administered to an animal for treating a disease, is sufficient to effect such treatment for the disease.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

"Treatment" or "treating" with respect to combination therapy i.e., use with a biologic means any administration of a compound of the present invention and includes:
(1) preventing the immune response from occurring in an animal which may be predisposed to the immune response but does not yet experience or display the pathology or symptomatology of the immune response,
(2) inhibiting the immune response in an animal that is experiencing or displaying the pathology or symptomatology of the immune response (i.e., arresting further development of the pathology and/or symptomatology), or
(3) ameliorating the immune response in an animal that is experiencing or displaying the pathology or symptomatology of the immune response (i.e., reducing in degree or severity, or extent or duration, the overt manifestations of the immune response or reversing the pathology and/or symptomatology e.g., reduced binding and presentation of antigenic peptides by MHC class II molecules, reduced activation of T-cells and B-cells, reduced humoral and cell-mediated responses and, as appropriate to the particular immune response, reduced inflammation, congestion, pain, necrosis, reduced loss in the efficacy of a biologic agent, and the like).

PREFERRED EMBODIMENTS

Certain compounds of Formula (I) within the broadest scope set forth in the Summary of the Invention are preferred. For example:

A. One preferred group of compounds is that wherein $R^1$ and $R^2$ are hydrogen.
B. Another preferred group of compounds is that wherein $R^1$ and $R^2$ together with the carbon atom to which they are attached form cycloalkylene optionally substituted with one or two $R^b$ independently selected from alkyl or halo. Preferably, $R^1$ and $R^2$ together with the carbon atom to which they are attached form cyclopropylene, cyclobutylene, cyclopentylene, or cyclohexylene optionally substituted with groups described immediately above. More preferably, $R^1$ and $R^2$ together with the carbon atom to which they are attached form cyclopropylene, cyclopentylene, or cyclohexylene. Most preferably, $R^1$ and $R^2$ together with the carbon atom to which they are attached form cyclopropylene.

C. Yet another preferred group of compounds is that wherein $R^1$ and $R^2$ together with the carbon atom to which they are attached form heterocyclylalkylene optionally substituted with one to four $R^c$ independently selected from alkyl or halo or optionally substituted with one to three $R^c$ where two $R^c$ are independently selected from alkyl, halo, haloalkyl, or hydroxyl and the third $R^c$ is hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R$^{14}$, -alkylene-S(O)$_{n2}$—R$^{15}$, —COOR$^6$, -alkylene-COR$^{17}$, —CONR$^{18}$R$^{19}$, or -alkylene-CONR$^{20}$R$^{21}$ (where n2 is 0-2 and R$^{14}$-R$^{17}$, R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl) wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl. Preferably, $R^1$ and $R^2$ together with the carbon atom to which they are attached form pyrrolidinyl, piperidinyl, tetrahydropyranyl, tetrahydrothiopyranyl, tetrahydrofuranyl, tetrahydrothiopyran-4-yl-1-oxide, tetrahydrothiopyran-4-yl-1,1-dioxide, hexahydropyrimidinyl, or hexahydropyridazinyl optionally substituted as described above. More preferably, $R^1$ and $R^2$ together with the carbon atom to which they are attached form piperidin-4-yl substituted with one to four $R^c$ independently selected from alkyl or halo or optionally substituted with one or two $R^c$ are independently selected from alkyl, halo, or haloalkyl, and a third $R^c$ selected from aminoalkyl, acyl, aralkyl, alkoxycarbonyl, alkoxyalkyl, alkoxyalkyloxyalkyl, heterocyclyl, heterocyclylalkyl, -alkylene-CONR$^{20}$R$^{21}$, or cycloalkyl wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl. Most preferably, $R^1$ and $R^2$ together with the carbon atom to which they are attached form 1-cyclohexylpyrrolidin-3-yl, 1-ethyl-2,2-dimethylpyrrolidin-4-yl, 1-propyl-2-methoxycarbonylpiperidin-4-yl, 2-oxopyrrolidin-3-yl, 1-ethyl-2-oxopyrrolidin-3-yl, 1-(1-methylpiperidin-4-ylcarbonyl)piperidin-4-yl, 1-ethoxycarbonyl-piperidin-4-yl, 1-benzylazetidin-3-yl, tetrahydrothiopyran-4-yl-1-oxide, tetrahydrothiopyran-4-yl-1,1-dioxide or piperidin-4-yl optionally substituted at the 1-position with methyl, ethyl, propyl, n-butyl, n-pentyl, 3-dimethylaminopropyl, 4-dimethylaminobutyl, 3-morpholin-4-ylpropyl, 3-piperidin-1-yl-propyl, 3-(4-methylpiperazin-1-yl)propyl, 3-(1-methylpiperidin-4-yl)propyl, 4-morpholin-4-ylbutyl, 2-(2-methoxyethyloxy)ethyl, 4-methoxybutyl, 4-aminocarbonylbutyl, 3-aminocarbonylpropyl, 1-ethoxycarbonylpiperidin-4-yl, 1,1-dioxo-tetrahydrothiopyran-4-yl, hydroxy, 2,2,2-trifluoroethyl, tert-butyl, 1,2-dimethylpiperidin-4-yl, 1,2,6-trimethylpiperidin-4-yl, 1,2,2-trimethylpiperidin-4-yl, 1-methyl-2-oxopiperidin-4-yl, 1-methylpiperidin-3-yl, 1-tert-butoxycarbonylpiperidin-4-yl, 1-cyclohexylpiperidin-4-yl, 1-cyclopropylmethylpyrrolidin-3-yl, 1-benzylpyrrolidin-3-yl, 1-benzyloxycarbonylpyrrolidin-3-yl, pyrrolidin-3-yl, 1-hydroxypyrrolidin-3-yl, 1-methylpyrrolidin-3-yl, 1-ethypyrrolidin-3-yl, 1-n-propyl or n-butylpyrrolidin-3-yl. Particularly preferably, $R^1$ and $R^2$ together with the carbon atom to which they are attached form tetrahydrothiopyran-4-yl, tetrahydrothiopyran-4-yl-1-oxide, tetrahydrothiopyran-4-yl-1,1-dioxide, or tetrahydropyran-4-yl.

(a) Within the above preferred groups (A-C) and the more preferred groups contained therein, an even more preferred group of compounds is that wherein:

$R^4$ is aralkyl, heteroaralkyl, heterocyclylalkyl, or -alkylene-X$^1$—R$^{22}$ (wherein X$^1$ is —NR$^{23}$—, —O—, —S(O)$_{n3}$—, —CO—, —COO—, —OCO—, —NR$^{23}$CO—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$, or —NR$^{23}$SO$_2$NR$^{24}$— where R$^{23}$ and R$^{24}$ are independently hydrogen, alkyl, or acyl, n3 is 0-2, and R$^{22}$ is alkyl, haloalkyl, cycloalkyl, cycloalkylalkyl, aryl, aralkyl, heteroaryl, heteroaralkyl, heterocyclyl, or heterocyclylalkyl) wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl; and $R^3$ and $R^5$ are hydrogen.

Preferably, $R^4$ is benzyl, 4-methoxybenzyl, 4-dimethylaminobutyl, 2-dimethylaminocarbonylethyl, dimethylaminocarbonylmethyl, methoxycarbonylmethyl, 3,4-dichlorobenzyl, 2-chlorobenzyl, 4-ethoxybenzyl, 4-nitrobenzyl, biphen-4-ylmethyl, naphth-1-ylmethyl, naphth-2-ylmethyl, 4-chlorobenzyl, 3-chlorobenzyl, 4-fluorobenzyl, 2-phenethyl, 4-hydroxybenzyl, 2-(4-hydroxyphenyl)ethyl, 2,6-difluorobenzyl, 2,2-difluoro-3-phenylpropyl, 2,2-dichloro-3-phenylpropyl, biphenyl-3-ylmethyl, 3-phenylpropyl, or 2,2-dimethyl-3-phenylpropyl and R$^3$ and R$^5$ are hydrogen.

Preferably, $R^4$ is -alkylene-S(O)$_{n3}$—R$^{22}$ where n3 is 0-2 and R$^{22}$ is alkyl, cycloalkylalkyl, aryl, aralkyl, heteroaryl, or heteroaralkyl wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl, preferably ethylthiomethyl, ethylsulfinylmethyl, ethylsulfonylmethyl, isopropylthiomethyl, 2-methylthioethyl, 2-methylsulfinylethyl, 2-methysulfonylethyl, 2-methylpropylsulfonylmethyl, isobutylsulfanylmethyl, tert-butylthiomethyl, benzenesulfonylmethyl, 2-phenylsulfanylethyl, 2-phenylsulfonylethyl, naphth-2-ylmethanesulfonylmethyl, biphenyl-2-ylmethanesulfonylmethyl, biphenyl-4-ylmethanesulfonylmethyl, phenylmethanesulfanylmethyl, phenylmethanesulfinylmethyl, phenylmethanesulfonylmethyl, 2-phenylmethanesulfonylethyl, 4-tert-butylphenylmethanesulfonylmethyl, 2-fluorophenylmethanesulfanylmethyl, 2-fluoro-phenylmethanesulfonylmethyl, 3-fluorophenylmethanesulfonylmethyl, 4-fluorophenylmethanesulfonylmethyl, 2-chlorophenylmethanesulfanylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenylmethanesulfonylmethyl, 2-trifluoromethylphenylmethanesulfanylmethyl, 2-trifluoromethylphenylmethanesulfonylmethyl, 3-trifluoromethylphenylmethanesulfonylmethyl, 4-trifluoromethylphenylmethanesulfonylmethyl, 2-cyanophenylmethanesulfanylmethyl, 2-cyanophenylmethanesulfonylmethyl, 3-cyanophenylmethanesulfonylmethyl, 2-bromophenylmethanesulfonylmethyl, 2-nitrophenylmethanesulfanylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-(4-trifluoromethoxybenzenesulfonyl)ethyl, 2-(3-trifluoromethoxybenzenesulfonyl)ethyl, 2-(2-trifluoromethoxybenzenesulfonyl)ethyl, 2-difluoromethoxyphenylmethanesulfonylmethyl, 3-difluoromethoxyphenylmethanesulfonylmethyl, 4-difluoromethoxyphenylmethanesulfonylmethyl, 2-(4-difluoromethoxybenzenesulfonyl)ethyl, 2-(2-difluoromethoxybenzenesulfonyl)ethyl, 2-(3-difluoromethoxybenzenesulfonyl)ethyl, 3-chloro-2-fluorophenylmethanesulfonylmethyl, 3,5-dimethylphenylmethanesulfonylmethyl, 3,5-bis-trifluoromethylphenylmethanesulfonylmethyl, 2,5-difluorophenylmethanesulfonylmethyl, 2,6-difluorophenylmethanesulfonylmethyl, 2,3-difluorophenylmethanesulfonylmethyl, 3,4-difluorophenylmethanesulfonylmethyl, 2,4-difluorophenylmethanesulfonylmethyl, 2,5-dichlorophenylmethanesulfonylmethyl, 3,4-dichlorophenylmethanesulfonylmethyl, 2,6-dichlorophenylmethanesulfonylmethyl, 2-fluoro-3-methylphenylmethanesulfonylmethyl, 4-fluoro-2-trifluoromethoxyphenylmethanesulfonylmethyl, 2-fluoro-6-trifluoromethylphenylmethanesulfonylmethyl, 2-fluoro-3-trifluoromethylphenylmethanesulfonylmethyl, 2-fluoro-4-trifluoromethylphenylmethanesulfonylmethyl, 2-fluoro-5-trifluoromethylphenylmethanesulfonylmethyl, 4-fluoro-3-trifluoromethylphenylmethanesulfonylmethyl, 2-chloro-5-trifluoromethylphenylmethane-sulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonylmethyl, 3,4,5-trimethoxyphenylmethanesulfonylmethyl, pyridin-2-ylmethanesulfonylmethyl, pyridin-3-ylmethanesulfonylmethyl, pyridin-4-ylmethanesulfonylmethyl, 2-(pyridin-2-ylsulfonyl)ethyl, 2-(pyridin-4-ylsulfonyl)ethyl, 1-oxypyridin-2-ylmethanesulfonylmethyl, cyclohexylmethanesulfanylmethyl, cyclohexylsulfinylmethyl, cyclohexylmethanesulfonylmethyl, cyclopropylmethanesulfonylmethyl, thiophen-2-ylsulfonylmethyl, 5-chlorothien-2-ylmethanesulfonylmethyl, or 3,5-dimethyl-isoxazol-4-ylmethanesulfonylmethyl, preferably 2-(difluoromethoxy)phenylmethane-sulfonylmethyl and $R^3$ and $R^5$ are hydrogen.

Preferably, $R^4$ is 1-ethoxycarbonylpiperidin-4-ylmethyl, 1-methylpiperidin-4-ylmethyl, 2-tetrahydropyran-4-ylethyl, pyrrolidin-1-ylmethyl, piperidin-1-ylmethyl, morpholin-4-ylmethyl, 2-morpholin-4-ylethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothiopyran-4-ylmethyl, 1,1-dioxotetrahydrothiopyran-4-ylmethyl, 1-methylpiperazin-4-ylmethyl, benzyloxymethyl, ethoxymethyl, isopropyloxymethyl, 2-dimethylaminoethyl, 2-piperidin-1-yl-ethyl, 2-pyrrolidin-1-ylethyl, tert-butyloxymethyl, imidazol-4-ylmethyl, indol-3-ylmethyl, 2-pyrrolidin-1-ylcarbonylethyl, pyrrolidin-1-ylcarbonylmethyl, indol-2-ylmethyl, 1-benzyl-imidazol-4-ylmethyl, 4-ethyl-4-methylpiperidin-1-ylmethyl, indol-1-ylmethyl, 1-methyl-piperidin-2-ylmethyl, 2,2,-difluoro-3-thien-2-ylmethyl, or pyridin-4-ylmethyl and $R^3$ and $R^5$ are hydrogen.

Most preferably, $R^4$ is isopropylsulfonylmethyl, cyclopropylmethanesulfonylmethyl, or 2-difluoromethoxyphenylmethanesulfonylmethyl; and
$R^3$ and $R^5$ are hydrogen.
(b) Within the above preferred groups (A-C) and the more preferred groups contained therein, another even more preferred group of compounds is that wherein:
$R^4$ is 1-methylcyclopentylmethyl or 1-methylcyclohexylmethyl; and
$R^3$ and $R^5$ are hydrogen.
(c) Within the above preferred groups (A-C) and the more preferred groups contained therein, yet another even more preferred group of compounds is that wherein:
$R^4$ is -alkylene-S(O)$_{n3}$-heteroaralkyl wherein n3 is 0-3 and the aromatic ring is optionally substituted with one, two, or three $R^d$ independently selected from alkyl, haloalkyl, alkoxy, hydroxy, haloalkoxy, halo, nitro, cyano, carboxy, or alkoxycarbonyl. Preferably, 4-trifluoro-methylpyridin-2-ylmethane-sulfonylmethyl, pyridin-2-ylmethanesulfonylmethyl, pyridin-3-ylmethanesulfonylmethyl, pyridin-4-ylmethanesulfonylmethyl, pyrimidinylmethanesulfanylmethyl, pyrimidinylmethanesulfinylmethyl, pyrimidinylmethanesulfonylmethyl, pyrazinylmethanesulfanylmethyl, pyrazinylmethanesulfinylmethyl, pyrazinylmethanesulfonylmethyl, pyridazinylmethanesulfanylmethyl, pyridazinylmethanesulfinylmethyl, or pyridazinylmethanesulfonylmethyl, preferably pyrazin-2-ylmethanesulfonylmethyl; and
$R^3$ and $R^5$ are hydrogen.
(d) Within the above preferred groups (A-C) and the more preferred groups contained therein, yet another even more preferred group of compounds is that wherein:
$R^4$ is -alkylene-SO$_2$—$R^{22}$ where $R^{22}$ is heterocyclyl wherein the heterocyclyl ring is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl. Preferably, the heterocycloalkyl is piperazin-1-yl, piperidin-1-yl, pyrrolidin-1-yl, morpholin-4-yl, or thiomorpholin-4-yl optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl, more preferably one or two $R^d$ independently selected from alkyl, haloalkyl, alkoxy, hydroxy, haloalkoxy, or halo.
(1) Within the above preferred, more preferred, and even more preferred groups above i.e., A, A(a-d), B, B(a-d), C and C(a-d), and preferred groups contained therein, a particularly preferred group of compounds is that wherein:
$R^6$ is —CF$_2$—$X^2$—$R^{25}$ where $X^2$ is —O— or —S(O)$_{n4}$— where n4 is 0-2 and $R^{25}$ is aryl or heteroaryl optionally substituted with one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl. Preferably, $X^2$ is —O— and $R^{25}$ is phenyl or heteroaryl (more preferably pyrimidinyl or pyridinyl) optionally substituted with one or two $R^e$ independently selected from alkyl, halo, hydroxy, alkoxy, alkoxyalkyl, haloalkoxy, cyano, nitro, carboxy, alkoxycarbonyl, alkylsulfonyl, or aminosulfonyl. Even more preferably, $R^{25}$ is phenyl or pyridinyl optionally substituted with $R^e$ selected from methyl, chloro, fluoro, hydroxy, methoxy, trifluoromethoxy, cyano, carboxy, methylsulfonyl, methoxycarbonyl, or —SO$_2$NH$_2$.

(2) Within the above preferred, more preferred, and even more preferred groups above i.e., A, A(a-d), B, B(a-d), C and C(a-d), and preferred groups contained therein, a particularly preferred group of compounds is that wherein:

R$^6$ is —CF$_2$—X$^2$—R$^{25}$ where X$^2$ is a single bond and R$^{25}$ is aryl or heteroaryl optionally substituted with one, two, or three R$^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl. Preferably, R$^{25}$ is phenyl or heteroaryl (more preferably pyrimidinyl or pyridinyl) optionally substituted with one or two R$^e$ independently selected from alkyl, halo, hydroxy, alkoxy, alkoxyalkyl, haloalkoxy, cyano, nitro, carboxy, alkoxycarbonyl, alkylsulfonyl, or aminosulfonyl. Even more preferably, R$^{25}$ is phenyl or pyridinyl optionally substituted with R$^e$ selected from methyl, chloro, fluoro, hydroxy, methoxy, trifluoromethoxy, cyano, carboxy, methylsulfonyl, methoxycarbonyl, or —SO$_2$NH$_2$.

(3) Within the above preferred, more preferred, and even more preferred groups above i.e., A, A(a-d), B, B(a-d), C and C(a-d), and preferred groups contained therein, a particularly preferred group of compounds is that wherein:

R$^6$ is —CF$_2$—X$^2$—R$^{25}$ where X$^2$ is a single bond and R$^{25}$ is alkyl, haloalkyl, cycloalkyl, or cycloalkylalkyl wherein the alicyclic ring is optionally substituted with one or two R$^e$ independently selected from alkyl or halo. Preferably, R$^{25}$ is methyl, trifluoromethyl, trifluoroethyl, cyclopropyl, cyclopropylmethyl, cyclohexyl, or cyclohexylmethyl wherein the alicyclic ring is optionally substituted with one or two R$^e$ independently selected from alkyl or halo.

(4) Within the above preferred, more preferred, and even more preferred groups above i.e., A, A(a-d), B, B(a-d), C and C(a-d), and preferred groups contained therein, a particularly preferred group of compounds is that wherein:

R$^6$ is —CF$_2$—X$^2$—R$^{25}$ where X$^2$ is —O— or —S(O)$_{n4}$— where n4 is 0-2 and R$^{25}$ is alkyl, haloalkyl, cycloalkyl, or cycloalkylalkyl wherein the alicyclic ring is optionally substituted with one or two R$^e$ independently selected from alkyl or halo. Preferably, X$^2$ is —O— and R$^{25}$ is methyl, trifluoromethyl, trifluoroethyl, cyclopropyl, cyclopropylmethyl, cyclohexyl, or cyclohexylmethyl wherein the alicyclic ring is optionally substituted with one or two R$^e$ independently selected from alkyl or halo.

Within the above preferred, more preferred, and even more preferred groups above i.e., A, A(a-d), A(a-d)(1), A(a-d)(2), A(a-d)(3), A(a-d)(4), B, B(a-d), B(a-d)(1), B(a-d)(2), B(a-d)(3), B(a-d)(4), C, C(a-d), C(a-d)(1), and C(a-d)(2), C(a-d)(3), C(a-d)(4), and preferred groups contained therein, most preferred group of compounds is that wherein:

R$^7$ is alkyl, more preferably methyl, ethyl, or 2-propyl.

Within the above preferred, more preferred, and even more preferred groups above i.e., A, A(a-d), A(a-d)(1), A(a-d)(2), A(a-d)(3), A(a-d)(4), B, B(a-d), B(a-d)(1), B(a-d)(2), B(a-d)(3), B(a-d)(4), C, C(a-d), C(a-d)(1), and C(a-d)(2), C(a-d)(3), C(a-d)(4), and preferred groups contained therein, most preferred group of compounds is that wherein:

R$^7$ is haloalkyl, preferably trifluoromethyl.

Within the above preferred, more preferred, and even more preferred groups above i.e., A, A(a-d), A(a-d)(1), A(a-d)(2), A(a-d)(3), A(a-d)(4), B, B(a-d), B(a-d)(1), B(a-d)(2), B(a-d)(3), B(a-d)(4), C, C(a-d), C(a-d)(1), and C(a-d)(2), C(a-d)(3), C(a-d)(4), and preferred groups contained therein, most preferred group of compounds is that wherein:

R$^7$ is phenyl optionally substituted with one, two, or three R$^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl wherein the aromatic or alicyclic ring in R$^g$ is optionally substituted with one, two, or three R$^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl. Preferably, phenyl optionally substituted with one, two, or three R$^e$ independently selected from alkyl, halo, haloalkyl, haloalkoxy, alkoxy, or alkylsulfonyl. More preferably, R$^7$ is 4- or 3,4-difluorophenyl.

Within the above preferred, more preferred, and even more preferred groups above i.e., A, A(a-d), A(a-d)(1), A(a-d)(2), A(a-d)(3), A(a-d)(4), B, B(a-d), B(a-d)(1), B(a-d)(2), B(a-d)(3), B(a-d)(4), C, C(a-d), C(a-d)(1), and C(a-d)(2), C(a-d)(3), C(a-d)(4), and preferred groups contained therein, most preferred group of compounds is that wherein:

R$^7$ is heteroaryl optionally substituted with one, two, or three R$^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl wherein the aromatic or alicyclic ring in R$^g$ is optionally substituted with one, two, or three R$^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl. Preferably, pyridinyl, thiophenyl, furanyl, or pyrrolyl optionally substituted with one or two R$^e$ independently selected from alkyl, halo, haloalkyl, haloalkoxy, alkoxy, or alkylsulfonyl.

(D) Yet another preferred group of compounds of Formula (I) is that wherein R$^6$ is —CF$_2$—X$^2$—R$^{25}$ where X$^2$ is —O— or —S(O)$_{n4}$— where n4 is 0-2 and R$^{25}$ is aryl or heteroaryl optionally substituted with one, two, or three R$^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl. Preferably, X$^2$ is —O— and R$^{25}$ is phenyl or heteroaryl (more preferably pyrimidinyl or pyridinyl) optionally substituted with one or two R$^e$ independently selected from alkyl, halo, hydroxy, alkoxy, alkoxyalkyl, haloalkoxy, cyano, nitro, carboxy, alkoxycarbonyl, alkylsulfonyl, or aminosulfonyl. Even more preferably, R$^{25}$ is phenyl or pyridinyl optionally substituted with R$^e$ selected from methyl, chloro, fluoro, hydroxy, methoxy, trifluoromethoxy, cyano, carboxy, methylsulfonyl, methoxycarbonyl, or —SO$_2$NH$_2$;

R$^7$ is phenyl or heteroaryl optionally substituted with one, two, or three R$^e$ independently selected from alkyl, halo, haloalkyl, haloalkoxy, alkoxy, or alkylsulfonyl, preferably 4-fluorophenyl, 3,4-difluorophenyl, or thiophen-3-yl; and R$^3$ and R$^5$ are hydrogen.

(E) Yet another preferred group of compounds of Formula (I) is that wherein:

$R^6$ is —$CF_2$—$X^2$—$R^{25}$ where $X^2$ is a single bond and $R^{25}$ is aryl or heteroaryl optionally substituted with one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl. Preferably, $R^{25}$ is phenyl or heteroaryl (more preferably pyrimidinyl or pyridinyl) optionally substituted with one or two $R^e$ independently selected from alkyl, halo, hydroxy, alkoxy, alkoxyalkyl, haloalkoxy, cyano, nitro, carboxy, alkoxycarbonyl, alkylsulfonyl, or aminosulfonyl. Even more preferably, $R^{25}$ is phenyl or pyridinyl optionally substituted with $R^e$ selected from methyl, chloro, fluoro, hydroxy, methoxy, trifluoromethoxy, cyano, carboxy, methylsulfonyl, methoxycarbonyl, or —$SO_2NH_2$;

$R^7$ is phenyl or heteroaryl optionally substituted with one, two, or three $R^e$ independently selected from alkyl, halo, haloalkyl, haloalkoxy, alkoxy, or alkylsulfonyl, preferably 4-fluorophenyl, 3,4-difluorophenyl, or thiophen-3-yl; and $R^3$ and $R^5$ are hydrogen.

(F) Yet another preferred group of compounds of Formula (I) is that wherein:

$R^6$ is —$CF_2$—$X^2$—$R^{25}$ where $X^2$ is a single bond and $R^{25}$ is alkyl, haloalkyl, cycloalkyl, or cycloalkylalkyl wherein the alicyclic ring is optionally substituted with one or two $R^e$ independently selected from alkyl or halo. Preferably, $R^{25}$ is methyl, trifluoromethyl, trifluoroethyl, cyclopropyl, cyclopropylmethyl, cyclohexyl, or cyclohexylmethyl wherein the alicyclic ring is optionally substituted with one or two $R^e$ independently selected from alkyl or halo;

$R^7$ is phenyl or heteroaryl optionally substituted with one, two, or three $R^e$ independently selected from alkyl, halo, haloalkyl, haloalkoxy, alkoxy, or alkylsulfonyl, preferably 4-fluorophenyl, 3,4-difluorophenyl, or thiophen-3-yl; and $R^3$ and $R^5$ are hydrogen.

(G) Yet another preferred group of compounds of Formula (I) is that wherein:

$R^6$ is —$CF_2$—$X^2$—$R^{25}$ where $X^2$ is —O— or —$S(O)_{n4}$— where n4 is 0-2 and $R^{25}$ is alkyl, haloalkyl, cycloalkyl, or cycloalkylalkyl wherein the alicyclic ring is optionally substituted with one or two $R^e$ independently selected from alkyl or halo. Preferably, $X^2$ is —O— and $R^{25}$ is methyl, trifluoromethyl, trifluoroethyl, cyclopropyl, cyclopropylmethyl, cyclohexyl, or cyclohexylmethyl wherein the alicyclic ring is optionally substituted with one or two $R^e$ independently selected from alkyl or halo;

$R^7$ is phenyl or heteroaryl optionally substituted with one, two, or three $R^e$ independently selected from alkyl, halo, haloalkyl, haloalkoxy, alkoxy, or alkylsulfonyl, preferably 4-fluorophenyl, 3,4-difluorophenyl, or thiophen-3-yl; and $R^3$ and $R^5$ are hydrogen.

Within the above groups (D)-(G) and the more preferred groups contained therein, an even more preferred group of compounds is that wherein:

$R^1$ and $R^2$ are hydrogen or $R^1$ and $R^2$ together with the carbon atom to which they are attached form cycloalkylene or heterocycloalkylene, preferably cyclopropylene, tetrahydrothiofuran-2-yl, tetrahydrofuran-4-yl, or 1,1-dioxotetrahydrothiopyran-4-yl. More preferably $R^1$ and $R^2$ together with the carbon atom to which they are attached form cyclopropylene.

(i) Within the above preferred and more preferred groups, an particularly preferred group of compounds is that wherein:

$R^4$ is -alkylene-$S(O)_2$—$R^{22}$ where $R^{22}$ is alkyl, aralkyl, heteroaralkyl, or cycloalkylalkyl wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl. Preferably $R^4$ is phenylmethanesulfonylmethyl, 4-tert-butylphenylmethanesulfonylmethyl, 2-fluorophenylmethanesulfonylmethyl, 3-fluorophenylmethanesulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonylmethyl, 4-trifluoromethoxyphenylmethanesulfonylmethyl, 2-trifluoromethylphenylmethanesulfonylmethyl, 3-trifluoromethylphenylmethanesulfonylmethyl, 4-trifluoromethylphenylmethanesulfonylmethyl, 2-cyanophenylmethanesulfonylmethyl, 3-cyanophenylmethanesulfonylmethyl, 2-bromophenylmethanesulfonylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-difluoromethoxyphenylmethanesulfonylmethyl, 3-difluoromethoxyphenylmethanesulfonylmethyl, 4-difluoromethoxyphenylmethanesulfonylmethyl, 3-chloro-2-fluorophenylmethanesulfonylmethyl, 3,5-dimethylphenylmethanesulfonylmethyl, 3,5-bis-trifluoromethylphenylmethanesulfonylmethyl, 2,5-difluorophenylmethanesulfonylmethyl, 2,6-difluorophenylmethanesulfonylmethyl, 2,3-difluorophenylmethanesulfonylmethyl, 3,4-difluorophenylmethanesulfonylmethyl, 2,4-difluorophenylmethanesulfonylmethyl, 2,5-dichlorophenylmethanesulfonylmethyl, 3,4-dichlorophenylmethanesulfonylmethyl, 2,6-dichlorophenylmethanesulfonylmethyl, 2-fluoro-3-methylphenylmethanesulfonylmethyl, 4-fluoro-2-trifluoromethoxyphenylmethanesulfonylmethyl, 2-fluoro-6-trifluoromethylphenylmethanesulfonylmethyl, 2-fluoro-3-trifluoromethylphenyl-methanesulfonylmethyl, 2-fluoro-4-trifluoromethylphenylmethanesulfonylmethyl, 2-fluoro-5-trifluoromethylphenylmethanesulfonylmethyl, 4-fluoro-3-trifluoromethylphenylmethanesulfonylmethyl, 2-chloro-5-trifluoromethyl-phenylmethanesulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonylmethyl, 3,4,5-trimethoxyphenylmethanesulfonylmethyl, pyridin-2-ylmethanesulfonylmethyl, pyridin-3-ylmethanesulfonylmethyl, pyridin-4-ylmethanesulfonylmethyl, N-oxypyridin-2-ylmethanesulfonylmethyl, 2-trifluoropyridin-6-ylmethanesulfonylmethyl, pyrazin-2-ylmethanesulfonylmethyl, cyclohexylmethanesulfonylmethyl, cyclohexylmethanesulfonylmethyl, cyclopropylmethanesulfonylmethyl, thiophene-2-sulfonylmethyl, 5-chlorothien-2-ylmethanesulfonylmethyl, or 3,5-dimethyl-isoxazol-4-ylmethanesulfonylmethyl. Even more preferably, $R^4$ is cyclopropylmethanesulfonylmethyl, 2-difluoromethoxyphenylmethanesulfonylmethyl, pyrazinylmethanesulfonylmethyl, or pyrimidinylmethanesulfonylmethyl, pyridinylmethanesulfonylmethyl; and the stereochemistry at the carbon to which $R^4$ is attached is (R) and to which $R^6$ is attached is (S).

(ii) Within the above preferred groups (D)-(G) and the more preferred groups contained therein, yet another even more preferred group of compounds is that wherein:

$R^4$ is -alkylene-$SO_2$—$R^{22}$ where $R^{22}$ is heterocyclyl wherein the heterocyclyl ring is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl. Preferably, the $R^7$ is phenyl or heteroaryl optionally substituted with one, two, or three $R^e$ independently selected from alkyl, halo, haloalkyl, haloalkoxy, alkoxy, or alkylsulfonyl, preferably 4-fluorophenyl, 3,4-difluorophenyl, or thiophen-3-yl;

$R^3$ and $R^5$ are hydrogen; and $R^4$ is cyclopropylmethansulfonylmethyl.

Reference to the preferred embodiments set forth above is meant to include all combinations of particular and preferred groups unless stated otherwise.

Representative compounds of Formula (I) are disclosed in Table I.

Compounds of Formula (I) where $R^3$ and $R^5$ are hydrogen, $R^1$, $R^2$, $R^4$, $R^6$ and $R^7$ are as defined in Table I below are:

TABLE I (I)

| Stereochem at (*C, **C) | $R^4$ | $R^6$ | $R^7$ | $R^1 + R^2$ |
|---|---|---|---|---|
| (S, R) | cyclopropylmethansulfonylmethyl | —$CF_2$—O-(4-F-phenyl) | 4-F-phenyl | cyclopropylene |
| (S, R) | cyclopropylmethansulfonylmethyl | —$CF_2$—O-(4-F-phenyl) | 4-F-phenyl | tetrahydrothio-pyran-4-yl |
| (S, R) | cyclopropylmethansulfonylmethyl | —$CF_2$—O-(4-F-phenyl) | 4-F-phenyl | 1,1-dioxohexahydro-1$\lambda^6$-thiopyran-4-yl |
| (S, R) | cyclopropylmethansulfonylmethyl | —$CF_2$—S-(4-F-phenyl) | 4-F-phenyl | cyclopropylene |
| (S, R) | cyclopropylmethansulfonylmethyl | —$CF_2$—$SO_2$-(4-F-phenyl) | 4-F-phenyl | cyclopropylene |
| (S, R) | cyclopropylmethansulfonylmethyl | —$CF_2$—O-(3-$OCH_3$-phenyl) | 4-F-phenyl | cyclopropylene |
| (S, R) | cyclopropylmethansulfonylmethyl | —$CF_2$—O-(4-F-phenyl) | thiophen-3-yl | cyclopropylene |
| (S, R) | cyclopropylmethansulfonylmethyl | —$CF_2$—O-(4-$SO_2CH_3$-phenyl) | 4-F-phenyl | cyclopropylene |
| (S, S) | 2,2-dimethylpropyl | —$CF_2$-pyridin-3-yl | 4-F-phenyl | cyclopropylene |
| (S, S) | 2,2-dimethylpropyl | —$CF_2$-pyridin-3-yl | thiophen-3-yl | cyclopropylene |
| (S, R) | cyclopropylmethansulfonylmethyl | —$CF_2$-(4-F-phenyl) | 4-F-phenyl | cyclopropylene |
| (S, R) | cyclopropylmethansulfonylmethyl | —$CF_2$-(4-F-phenyl) | 4-F-phenyl | 1,1-dioxohexa-hydro-1$\lambda^6$-thiopyran-4-yl |
| (S, R) | cyclopropylmethansulfonylmethyl | —$CF_2$—O-pyridin-3-yl | 4-F-phenyl | cyclopropylene |
| (S, R) | cyclopropylmethansulfonylmethyl | —$CF_2$—O-(2-$CH_3$-pyridin-5-yl) | 4-F-phenyl | cyclopropylene | heterocycloalkyl is piperazin-1-yl, piperidin-1-yl, pyrrolidin-1-yl, morpholin-4-yl, or thiomorpholin-4-yl optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl, more preferably one or two $R^d$ independently selected from alkyl, haloalkyl, alkoxy, hydroxy, haloalkoxy, or halo.

(H) Yet another preferred group of compounds of Formula (I) is that wherein:

$R^1$ and $R^2$ are cycloalkylene or heterocycloalkylene, preferably cyclopropylene, tetrahydrothiopyran-2-yl, 1,1-dioxohexahydrothiopyranyl, or tetrahydropyran-4-yl;

$R^6$ is —$CF_2$—O—$R^6$, —$CF_2$—S—$R^6$, or —$CF_2$—$SO_2$—$R^6$ wherein $R^6$ is phenyl or heteroaryl (preferably pyridinyl) optionally substituted with one, two, or three alkyl, halo, hydroxyl, alkoxy, haloalkoxy alkylsulfonyl, or aminosulfonyl, preferably methyl, fluoro, hydroxyl, methoxy, trifluoromethoxy, or methylsulfonyl, more preferably $R^6$ is 4-fluorophenyl, 3-methoxyphenyl, 4-methylsulfonylphenyl, pyridin-3-yl, or 2-methylpyridin-5-yl; and General Synthetic Scheme Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1999.

Compounds of Formula (I) where $R^1$, $R^2$, $R^3$, $R^4$, $R^5$, and $R^7$ are as defined in the Summary of the Invention and $R^6$ is $-CF_2-X^2-R^{25}$ where $X^2$ is a single bond, $-O-$ or $-S(O)_{n4}-$ where n4 and $R^{25}$ are as defined in the Summary of the Invention can be prepared by proceeding as illustrated and described in Scheme 1 below.

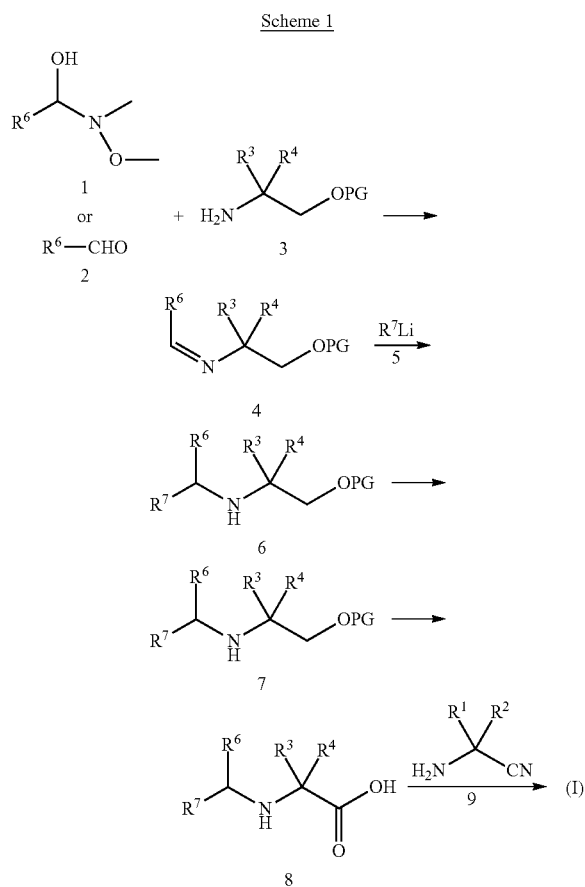

Scheme 1

Reaction of a compound of formula 1 or 2 where $R^6$ is as defined in the Summary of the Invention with an aminoethanol compound of formula 3 where $R^3$ and $R^4$ are as defined in the Summary of the Invention and PG is a suitable oxygen protecting group utilizing Dean Stark apparatus provides an imine compound of formula 4. Suitable oxygen protecting groups include groups such as dimethylsilyl, dimethyl-tert-butylsilyl, and the like. Other suitable oxygen protecting groups and reaction conditions for putting them on can be found in Greene, T. W.; and Wuts, P. G. M.; *Protecting Groups in Organic Synthesis*; John Wiley & Sons, Inc. 1999.

Compounds of formula 1 and 2 can be prepared by methods well known in the art. Some such methods are disclosed in detail in working examples below. Compounds of formula 3 can also be prepared from corresponding natural and unnatural amino acids by reduction of the acid or ester group to alcoholic group, followed by protection of the alcoholic group by methods well known in the art. Some such procedures are described in PCT Application Publication No. WO 03/075836, the disclosure of which is incorporated herein by reference in its entirety.

Treatment of 4 with an organic lithium compound of formula $R^7Li$ where $R^7$ is as defined in the Summary of the Invention provides compound 6. Removal of the oxygen protecting group in 6, followed by oxidation of the resulting alcohol 7 provides a compound of formula 8. Reaction conditions for removing oxygen protecting groups can be found in Greene, T. W.; and Wuts, P. G. M.; *Protecting Groups in Organic Synthesis*; John Wiley & Sons, Inc. 1999. The conversion of alcohol 7 to acid 8 is carried out with a suitable oxidizing agent such as Jones oxidizing reagent or $H_5IO_6/CrO_3$, and the like.

Coupling of compound 8 with alpha-aminoacetonitrile compound of formula 9 provides a compound of Formula (I). The reaction is carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexylcarbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 8 into an active acid derivative such as succinimide ester and then reacting it with an amine of formula 9. The reaction typically requires 2 to 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

Alternatively, compounds of Formula (I) where $R^1$, $R^2$, $R^3$, $R^4$, $R^5$, and $R^7$ are as defined in the Summary of the Invention and $R^6$ is $-CF_2-R^{25}$ where $R^{25}$ is as defined in the Summary of the Invention can be prepared by proceeding as illustrated and described in Scheme 2 below.

Scheme 2

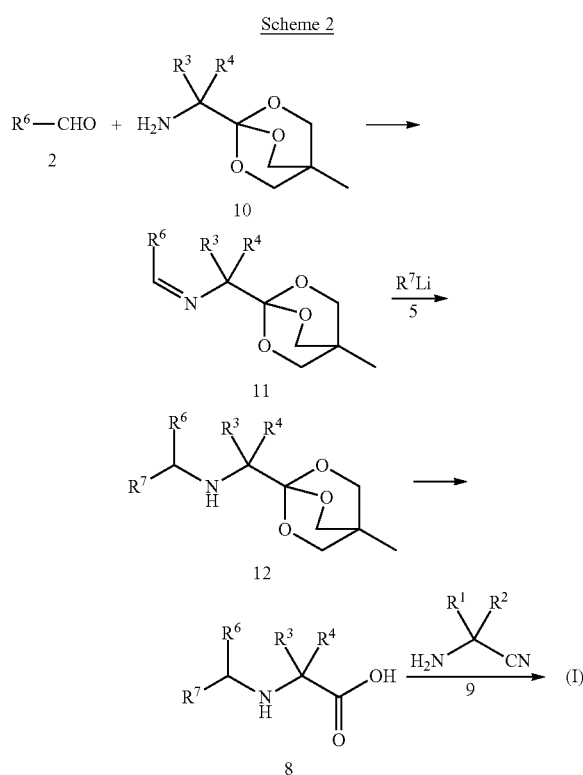

Reaction of a compound of formula 2 where $R^6$ is as defined in the Summary of the Invention with an amino compound of formula 10 where $R^3$ and $R^4$ are as defined in the Summary of the Invention utilizing Dean Stark apparatus provides an imine compound of formula 11. Compounds of formula 10 can be prepared by methods well known in the art. Some such methods are disclosed in detail in working examples below. Reaction of 11 with a compound of formula 5 provides a compound of formula 12. Removal of the 4-methyltrioxabicyclo[2.2.2]oct-1-yl group in 12 provides a compound of formula 8 which is then converted to a compound of Formula (I) as described in Scheme 1 above.

Alternatively, the compound of Formula (I) where $R^6$ is $-CF_2-X^2-R^{25}$ where $X^2$ is a single bond, $-O-$ or $-S(O)_{n4}-$ where n4 and $R^{25}$ is as defined in the Summary of the Invention can be prepared as illustrated and described in Scheme 3 below.

Scheme 3

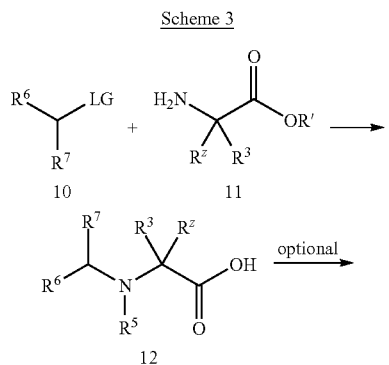

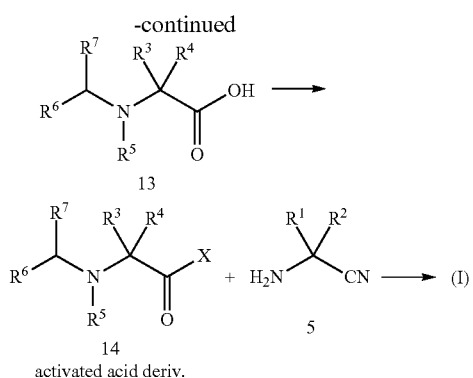

Reaction of a compound of formula 10 where LG is a suitable leaving group such as trifluoromethansulfonate, and the like, and $R^6$ and $R^7$ are as defined in Summary of the Invention with an alpha amino acid compound of formula 11 where $R^3$ and $R^5$ is as defined in the Summary of the Invention, preferably hydrogen, $R^z$ is $R^4$ as defined in the Summary of the Invention or -(alkylene)-$X^1$—Z where $X^1$ is as defined in the Summary of the Invention and Z is a protecting group e.g., trityl, and the like, and R' is hydrogen or a suitable carboxy protecting group such as alkyl, and the like, provides a compound of formula 12. The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Preferably, the reaction is carried out at room temperature. Other suitable carboxy protecting and Z groups and reaction conditions for putting them on and removing them can be found in Greene, T. W.; and Wuts, P. G. M.; *Protecting Groups in Organic Synthesis*; John Wiley & Sons, Inc. 1999, the disclosure of which is incorporated herein by reference in its entirety.

Compound of formula 10 can be prepared by methods well known in the art. For example, a compound of formula 10 where $R^6$ is $-CF_2-X^2-R^{25}$ where $X^2$ is $-O-$ or $-S-$ and $R^{25}$ is aryl or heteroaryl and $R^7$ is aryl can be prepared by reacting a compound of formula $R^6X^2CF_2COOR$ where $R^6$ and $X^2$ are as defined above and R is alkyl with $R^7Li$ where $R^7$ is aryl to form a compound of formula $C(O)R^7(-CF_2-X^2-R^{25})$ which upon reduction of the keto group provides corresponding alcohol of formula $C(OH)R^7(-CF_2-X^2-R^{25})$. The hydroxyl group in $C(OH)R^7(-CF_2-X^2-R^{25})$ is then converted to a suitable leaving group by methods well known in the art. For example, $CR^7(-X^2-R^{25})(OTf)$ can be readily prepared by reacting $CR^7(-X^2-R^{25})(OH)$ with triflic anhydride or trifluoromethanesulfonyl chloride in the presence of a suitable base such as sodium hydroxide, and the like.

A compound of formula 12 where $R^z$ is -(alkylene)-$X^1$—Z can be converted to a corresponding compound of formula 12 where $R^z$ is $R^4$ where $R^4$ is -(alkylene)-$X^1$—$R^{22}$ where $R^{22}$ is as defined in the Summary of the invention by methods well known in the art. For example, a compound of formula 12 where $X^1$ is $-S(O)_{n3}-$ where n3 is 0-2 and $R^z$ is trityl protecting group can be easily converted to a compound of formula 13 where $R^z$ is $R^4$ where $R^4$ is -(alkylene)-$S(O)_{n3}$—$R^{22}$ where $R^{22}$ is alkyl, cycloalkylalkyl, heterocyclylalkyl, aralkyl or heteroaralkyl by removing the trityl group and reacting the resulting thiol group with suitable alkylating agent of the formula $R^{22}LG$ where LG is a leaving group such as halo, tosylate, mesylate, triflate, and the like, in the presence of a base and optionally oxidizing the sulfur atom to sulfoxide or sulfone with an oxidizing agent such as OXONE®, and the like.

Similarly, other compounds of formula 12 where $R^z$ is $R^4$ where $R^4$ is -(alkylene)-$X^1$—$R^{22}$ where $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCOONR^{23}$, $NR^{23}CONR^{24}$—, or $NR^{23}SO_2NR^{24}$ where $R^{22}$, $R^{23}$ and $R^{24}$ are as defined in the Summary of the Invention can be prepared from commercially available compound amino acids such as lysine, glutamic acid, aspartic acid, serine, and homoserine by methods well known in the art. Some such methods are described in U.S. Pat. No. 6,136,844 the disclosure of which is incorporated herein by reference in its entirety.

Compounds of formula 11 are either commercially available or they can be prepared by methods well known in the art. For example, alanine, cysteine, aspartic acid, glutamic acid, phenylalanine, histidine, and lysine are commercially available. Others can be prepared by methods well known in the art. Some such methods are described in PCT Applications Publication Nos. WO 03/075836, WO 00/55144, WO 01/19816, WO 02/20485, WO 03/029200, U.S. Provisional Application No. 60/422,337, U.S. Pat. Nos. 6,353,017B1, 6,492,662B1, 353,017 B1 and 6,525,036B1, 6,229,011B1, 6,610,700, the disclosures of which are incorporated herein by reference in their entirety.

Removal of the carboxy protecting group from a compound of formula 12 where R' is a protecting group provides a compound of formula 13. The conditions used to remove the carboxy protecting group depend on the nature of the carboxy protecting group. For example, if R' is alkyl, it is removed under basic hydrolysis reaction conditions utilizing aqueous base such as aqueous lithium hydroxide, sodium hydroxide, and the like in an alcoholic solvent such as methanol, ethanol, and the like.

Compound 13 is then converted to an activated acid derivative 14 (X is a leaving group), which upon reaction with an aminoacetonitrile compound of formula 5 provides a compound of Formula (I). The activated acid derivative can be prepared and then reacted with compound 5 in a stepwise manner or the acid derivative can be generated in situ in the presence of compound 5. For example, if the activated acid is acid halide it is first prepared by reacting 12 (where R' is hydrogen) or 13 with a halogenating agent such as thionyl chloride, oxalyl, chloride and the like and then reacted with compound 5. Alternatively, the activated acid derivative is generated in situ by reacting compound 12 (where R' is hydrogen) or 13 and 5 in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Alternatively, the activated acid 14 can be reacted with $CR^1R^2(NH_2)CONH_2$ where $R^1$ and $R^2$ are as described in the Summary of the Invention, followed by conversion of the —$CONH_2$ group to the cyano group by methods well known in the art.

A compound of Formula (I) can be converted to other compounds of Formula (I). For example:

A compound of Formula (I) where $R^6$ is an aromatic ring substituted with halo can be reacted with appropriated boronic acid under palladium catalyzed Suzuki coupling reaction conditions to provide a correspond compound of Formula (I) where $R^6$ is further substituted with an aryl or heteroaryl ring.

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (I). A compound of Formula (I) containing a halo group such as chloro can be converted to a corresponding compound of Formula (I) containing an methylthio by treating it with sodium thiomethoxide. The methylthio group can be oxidized to methylsulfonyl using a suitable oxidizing agent such as OXONE®. A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

Preparation of Biological Agents

In practicing this invention several processes for the generation or purification of biological agents are used. Methods for preparing the biologics are well known in the art as discussed below.

Monoclonal antibodies are prepared using standard techniques, well known in the art, such as by the method of Kohler and Milstein, *Nature* 1975, 256:495, or a modification thereof, such as described by Buck et al. 1982, *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

Chimeric antibodies composed of human and non-human amino acid sequences may be formed from the mouse monoclonal antibody molecules to reduce their immunogenicity in humans (Winter et al. *Nature* 1991 349:293; Lobuglio et al. *Proc. Nat. Acad. Sci. USA* 1989 86:4220; Shaw et al. *J. Immunol.* 1987 138:4534; and Brown et al. *Cancer Res.* 1987 47:3577; Riechmann et al. *Nature* 1988 332:323; Verhoeyen et al. *Science* 1988 239:1534; and Jones et al. *Nature* 1986 321:522; EP Publication No. 519,596, published Dec. 23, 1992; and U.K. Patent Publication No. GB 2,276,169, published Sep. 21, 1994).

Antibody molecule fragments, e.g., F(ab').sub.2, FV, and sFv molecules, that are capable of exhibiting immunological binding properties of the parent monoclonal antibody molecule can be produced using known techniques. Inbar et al. *Proc. Nat. Acad. Sci. USA* 1972 69:2659; Hochman et al. *Biochem.* 1976 15:2706; Ehrlich et al. *Biochem.* 1980 19:4091; Huston et al. *Proc. Nat. Acad. Sci. USA* 1988 85 (16):5879; and U.S. Pat. Nos. 5,091,513 and 5,132,405, to Huston et al.; and U.S. Pat. No. 4,946,778, to Ladner et al.

In the alternative, a phage-display system can be used to expand the monoclonal antibody molecule populations in vitro. Saiki, et al. *Nature* 1986 324:163; Scharf et al. *Science* 1986 233:1076; U.S. Pat. Nos. 4,683,195 and 4,683,202; Yang et al. *J. Mol. Biol.* 1995 254:392; Barbas, III et al. *Methods: Comp. Meth Enzymol.* 1995 8:94; Barbas, III et al. *Proc. Natl. Acad. Sci. USA* 1991 88:7978.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. Nature 1978 275:615, Goeddel et al. *Nature* 1979 281:544, Goeddel et al. *Nucleic Acids Res.* 1980 8:4057, European Application No. EP 36,776, U.S. Pat. No. 4,551, 433, deBoer et al. *Proc. Natl. Acad. Sci. USA* 1983 80:21-25, and Siebenlist et al. *Cell* 1980 20:269.

Expression systems in yeast include those described in Hinnen et al. *Proc. Natl. Acad. Sci. USA* 1978 75:1929, Ito et al. *J. Bacteriol.* 1983 153:163, Kurtz et al. *Mol. Cell. Biol.* 1986 6:142, Kunze et al. *J. Basic Microbiol.* 1985 25:141, Gleeson et al. *J. Gen. Microbiol.* 1986 132:3459, Roggenkamp et al. *Mol. Gen. Genet.* 1986 202:302, Das et al. *J. Bacteriol.* 1984 158:1165, De Louvencourt et al. *J. Bacteriol.* 1983 154:737, Van den Berg et al. *Bio/Technology* 1990 8:135, Kunze et al. *J. Basic Microbiol.* 1985 25:141, Cregg et al. *Mol. Cell. Biol.* 1985 5:3376, U.S. Pat. Nos. 4,837,148 and 4,929,555, Beach et al. *Nature* 1981 300:706, Davidow et al. *Curr. Genet.* 1985 10:380, Gaillardin et al. *Curr. Genet.* 1985 10:49, Ballance et al. *Biochem. Biophys. Res. Commun.* 1983 112:284-289, Tilburn et al. *Gene* 1983 26:205-221, Yelton et al. *Proc. Natl. Acad. Sci. USA* 1984 81:1470-1474, Kelly et al. *EMBO J.* 1985 4:475-479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. *J. Gen. Virol.* 1988 69:765-776, Miller et al. *Ann. Rev. Microbiol.* 1988 42:177, Carbonell et al. *Gene* 1988 73:409, Maeda et al. *Nature* 1985 315:592-594, Lebacq-Verheyden et al. *Mol. Cell. Biol.* 1988 8:3129, Smith et al. *Proc. Natl. Acad. Sci. USA* 1985 82:8404, Miyajima et al. *Gene* 1987 58:273, and Martin et al. *DNA* 1988 7:99. Numerous baculoviral strains and variants and corresponding permissive insect host cells from hosts are described in Luckow et al. *Bio/Technol-* ogy 1988 6:47-55, Miller et al. *GENERIC ENGINEERING*, Setlow, J. K. et al. eds., Vol. 8, Plenum Publishing, pp. 1986 277-279, and Maeda et al. *Nature* 1985 315:592-594.

Mammalian expression can be accomplished as described in Dijkema et al. *EMBO J.* 1985 4:761, Gorman et al. *Proc. Natl. Acad. Sci. USA* 1982 79:6777, Boshart et al. *Cell* 1985 41:521, and U.S. Pat. No. 4,399,216. Other features of mammalian expression can be facilitated as described in Ham et al. *Meth. Enz.* 1979 58:44, Barnes et al. *Anal. Biochem.* 1980 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195.

The production of recombinant adenoviral vectors are described in U.S. Pat. No. 6,485,958.

Botulinum toxin type A can be obtained by establishing and growing cultures of *Clostridium botulinum* in a fermenter and then harvesting and purifying the fermented mixture in accordance with known procedures.

Any of the above-described protein production methods can be used to provide the biologic that would benefit from the present invention.

Pharmacology and Utility

The compounds of the invention are selective inhibitors of cysteine proteases, in particular, cathepsin S, K, B, and/or F, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1-5, infra.

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 20 milligram per kilogram body weight (mg/kg) per day, typically from about 100 μg/kg/day to about 10 mg/kg/day. Therefore, a therapeutically effective amount for an 80 kg human patient may range from about 1 mg/day to about 1.6 g/day, typically from about 1 mg/day to about 100 mg/day. In general, one of ordinary skill in the art, acting in reliance upon personal knowledge and the disclosure of this application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described in Example 1 below.

EXAMPLES

The present invention is further exemplified, but not limited by, the following examples that illustrate the preparation of compounds of Formula (I) (Examples) and intermediates (References) according to the invention.

Example A

Synthesis of 2(RS)-benzyloxycarbonylamino-4(RS)-(2-methoxyphenyl)pentanoic acid

To d,l-2-methoxy-α-methylbenzyl alcohol (0.5 g, 3.29 mmol) was added 48% aq. HBr (2 ml) and the reaction mixture was stirred rapidly for 1.5 h. The reaction mixture was diluted with hexane (30 ml), washed with water, dried with MgSO$_4$, filtered, and evaporated under vacuum. The crude d,l-2-methoxy-α-methylbenzyl bromide was added to a solution of tributyltin hydride (0.67 ml, 2.49 mmol), Z-dehydroalanine methyl ester (0.25 g, 1.06 mmol), and 2,2'-azobisisobutyronitrile (15 mg, 0.09 mmol) in benzene (5 ml). The reaction mixture was heated at 80° C. under a nitrogen atmosphere for 5 h. Benzene was removed under vacuum and the residue was dissolved in methanol (20 ml). 2N KOH (5 ml) was added and the mixture was rapidly stirred at room temperature over night. Methanol was removed under vacuum and the residue was diluted with water (20 ml). The aqueous solution was washed with ether to remove the tin by products. The aqueous layer was acidified with 6 N HCl (aq.) and the product was extracted with ethyl acetate. The combined organic layers were washed with brine, dried with MgSO$_4$, filtered, and evaporated under vacuum to give 2-benzyloxycarbonylamino-4-(2-methoxyphenyl)pentanoic acid (190 mg, 0.53 mmol) as a mixture of diastereomers in sufficiently pure form to be used without further purification. MS: (M$^+$+H) 358, (M$^+$−H) 356.

Following the procedure described above, and utilizing appropriate starting materials the following amino acids were prepared:

2-benzyloxy-carbonylamino-4-(2-methoxyphenyl)hexanoic acid;
2-benzyloxy-carbonylamino-4-(4-fluorophenyl)pentanoic acid;
2-benzyloxy-carbonylamino-4-(4-chlorophenyl)pentanoic acid;
2-benzyloxy-carbonylamino-4-(4-methoxyphenyl)pentanoic acid;
2-benzyloxy-carbonylamino-4-(2-trifluoromethylphenyl) pentanoic acid;
2-benzyloxy-carbonylamino-4-(3-trifluoromethylphenyl) pentanoic acid;
2-benzyloxy-carbonylamino-4-(napth-1-yl)pentanoic acid;
2-benzyloxy-carbonylamino-4-(2,6-dimethylphenyl)pentanoic acid;
2-benzyloxy-carbonylamino-4-(2,4-difluorophenyl)pentanoic acid;
2-benzyloxy-carbonylamino-4-(2,4-dimethylphenyl)pentanoic acid;
2-benzyloxy-carbonylamino-4-(2,5-dimethylphenyl)pentanoic acid; and
2-benzyloxy-carbonylamino-4-(2,4-dichlorophenyl)pentanoic acid.

The benzyloxycarbonyl group can be removed as described in Example B below to give the corresponding free amino acid.

Example B

Synthesis of 2(S)-2,6-difluorophenylalanine

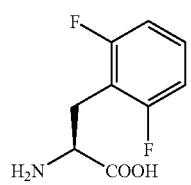

Step 1

N-(Benzyloxycarbonyl)-α-phosphonoglycine trimethyl ester (Aldrich No. 37, 635-3; 6.7 g, 20 mmol) and 1,8-diazabicyclo[5,4,0]undec-7-ene (Aldrich No. 13, 900-9; 3.3 ml, 22 mmol) were dissolved in methylene chloride (11 ml) and stirred at room temperature for 15 min, and then cooled to <−30° C. A solution of 2,6-difluorobenzaldehyde (1.9 ml, 20 mmol) in methylene chloride (25 ml) was added to the reaction mixture dropwise over 20 min. The reaction mixture was stirred for another 20 min, and then allowed to warm up to room temperature for 30 min. The reaction mixture was then poured into ethyl ether (300 ml) and washed with 1 N HCl, brine and dried over MgSO$_4$. Rotary evaporation gave crude 2-benzyloxycarbonylamino-3-(2,6-difluorophenyl) acrylic acid methyl ester which was purified by chromatography on a Medium Pressure Liquid Column (MPLC) eluting with 20% ethyl acetate/80% hexane to give pure product (5 g, 72% yield, liquid).

Step 2

A mixture of 2-benzyloxycarbonylamino-3-(2,6-difluorophenyl)acrylic acid methyl ester (14.4 mmol), and catalyst, (+)-1,2-bis-[(2S,5S)2,5-diethylphopholano]benzene (cyclooctadiene)rhodium (1) trifluoromethanesulfonate (Strem. Chemical No. 45-0151; 104 mg, 0.14 mmol) was dissolved in ethanol (150 ml). Hydrogenation was performed at 50 psi H$_2$ at room temperature over 2 days. The solvent was then removed by rotary evaporation to give 2(S)-benzyloxycarbonylamino-3-(2,6-difluorophenyl)propionic acid methyl ester.

Step 3

2(S)-Benzyloxycarbonylamino-3-(2,6-difluorophenyl) propionic acid methyl ester (5 g, 14.4 mmol) was dissolved in methanol (60 ml) and cooled on ice. 1 N NaOH (22 ml, 22 mmol) was added dropwise over 15 min. The reaction mixture was removed from cooling bath and stirring was continued at room temperature for 4 h. The solvent was then removed by rotary evaporation and the residue was treated with water (100 ml) and then with 1 N HCl to adjust the pH to 4. The product was extracted with ethyl acetate (300 ml, 200 ml). Evaporation of the solvent and crystallization of the residue from methylene chloride/hexane gave 2(S)-benzyloxycarbonylamino-3-(2,6-difluorophenyl)propionic acid (4.6 g, 13.7 mmol, 94% yield).

Step 4

2(S)-Benzyloxycarbonylamino-3-(2,6-difluorophenyl) propionic acid was hydrogenated at 50 psi in ethanol (25 ml) in the presence of 5% palladium on activated carbon (600 mg) for 24 h. The catalyst was removed by filtration through Celite® and the solvent evaporated to give a residue which was crystallized from ethyl ether to give 2(S)-2,6-difluorophenylalanine (2.2 g, 11 mmol, 80% yield). $^1$H NMR (DMSO-d$_6$): δ 7.28 (m, 1H), 7.0 (t, J=7.6 Hz, 2H), 2.77 (m, 2H). MS: 202.2 (M+1), 199.7 (M−1).

Example C

Synthesis of 2(RS)-amino-4-methyl-4-phenylpentanoic acid

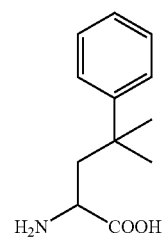

Step 1

4-Methyl-4-phenyl-1-pentene was prepared by reacting 2-phenyl-2-propanol with 3-(trimethylsilyl)propene by the method of Cella, *J. Org. Chem.*, 1982, 47, 2125-2130.

Step 2

4-Methyl-4-phenyl-1-pentene was ozonolyzed at −78° C. in dichloromethane followed by dimethyl sulfide quenching to give crude product which was purified by silica gel chromatography to give 3-methyl-3-phenylbutanal which was then converted to the title compound by proceeding as described in PCT application publication No. WO 2004/052921, Reference C, on page 68 of the application.

Example D

Synthesis of 2(S)-benzyloxycarbonylamino-3-pyrazol-1-ylpropionic acid

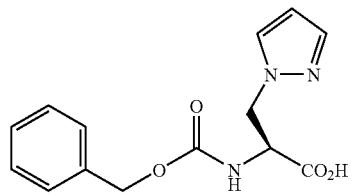

The title compound was prepared by treating S-benzyloxycarbonylserine-β-lactone with pyrazole in acetonitrile at 60° C. for 16 h (see *J. Am. Chem. Soc.*, 1985, 107, 7105-7109).

Following the procedure described above, but substituting pyrazole with [1.2.4]-triazole and [1.2.3]-triazole provided 2(S)-benzyloxycarbonylamino-3-[1.2.4]-triazol-1-ylpropionic acid and 2(S)-benzyloxycarbonylamino-3-[1.2.3]-triazol-1-ylpropionic acid respectively.

Example E

Synthesis of 2(S)-(tert-butoxycarbonyl)amino-3-thiazol-2-ylpropionic acid

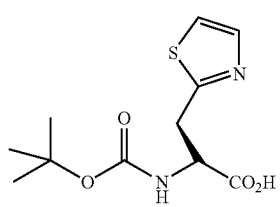

To 2-tert-butoxycarbonylamino-3-thiazol-2-ylpropionic acid methyl ester (500 mg, 1.75 mmol) in a mixture of acetonitrile (6 ml) and 0.2 M aqueous NaHCO$_3$ (12 ml) was added Alcalase (2.4 L, 0.08 ml), and the solution was stirred vigorously at room temperature for about 2.5 h. The reaction mixture was then evaporated at 30° C. to remove acetonitrile, and the aqueous residue was washed with ether. The aqueous phase was acidified with 6N HCl to pH 3 and the solution was extracted with ethyl acetate. The combined organic layers were then dried and evaporated to yield 2(S)-tert-butoxycarbonylamino-3-thiazol-2-ylpropionic acid (204 mg).

Reference F

Synthesis of 4-amino-4-cyano-1-ethylpiperidine

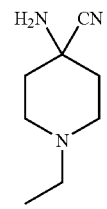

A mixture of 1-ethyl-4-piperidone (13.2 ml, 100 mmol), ammonium chloride (21.4 g, 400 mmol), sodium cyanide (19.6 g, 400 mmol) and water (550 ml) was stirred at room temperature for 48 h. The pH of the reaction mixture was adjusted to 10.1 and the product was extracted with ethyl acetate. The organic extracts were washed with brine and dried over magnesium sulfate. Rotary evaporation of the solvent gave a mixture of 4-amino-4-cyano-1-ethylpiperidine and 4-hydroxy-4-cyano-1-ethylpiperidine (7.67 g). This mixture of products was treated with 7M ammonia in methanol (20 ml) and allowed to stand at room temperature for 24 h. The methanol and excess ammonia were removed in vacuo and the residue was cooled to give 4-amino-4-cyano-1-ethylpiperidine as a crystalline solid (7.762 g).

Reference G

Synthesis of 2(S)-benzyloxycarbonylamino-3-(1-methylcyclopentyl)propionic acid

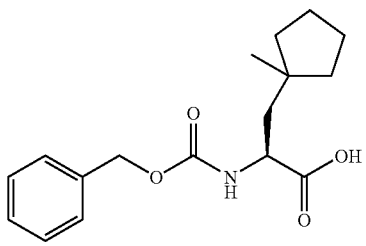

Step 1

1-Methylcyclopentanol (20 g, 0.2 mol) was added to hydrobromic acid (40 ml) at room temperature. After stirring for 1 h, the solution was extracted with hexane and the hexane was washed with brine and dried with magnesium sulfate. After concentration of the organic layer, 20.5 g of 1-methylcyclopentyl bromide was obtained.

Step 2

Tributyltin hydride (37.8 g, 130 mmol) was added at reflux to a 500 ml of flask charged with benzene (200 ml) was added Z-dehydro-Ala methyl ester (15 g, 64 mmol), 1-methylcyclopentyl bromide (20.5 g) and AIBN (1.9 g). After 2 h, the solvent was removed and the residue was purified by column chromatograph to yield 2-benzyloxycarbonylamino-3-(1-methylcyclopentyl)propionic acid methyl ester (7.9 g).

Step 3

2-Benzyloxycarbonylamino-3-(1-methylcyclopentyl)propionic acid methyl ester (7.6 g, 23.8 mmol) was dissolved in a mixture of acetonitrile (82 ml) and 0.2 M aqueous NaHCO$_3$ (158 ml) and Alcalase 2.4 L (1.1 ml) was added and the reaction mixture was stirred vigorously for 8 h. The reaction mixture was then evaporated at 30° C. to remove acetonitrile, and the aqueous residue was washed with ether. The ethereal layer was concentrated to yield (R)-2-benzyloxycarbonylamino-3-(1-methylcyclopentyl)propionic acid methyl ester (1.9 g). The aqueous phase was filtered with Celite®, the pH was adjusted to 3 with 6N HCl, and the solution was extracted with ethylacetate. The ethyl acetate layer was dried and evaporated to yield 2(S)-benzyloxycarbonylamino-3-(1-methylcyclopentyl)propionic acid (1.4 g).

Reference H

Synthesis of 1-aminocyclopropanecarbonitrile hydrochloride

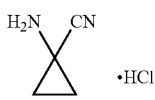

Step 1

A mixture of benzophenone imine (25 g, 0.138 mol, Aldrich) and aminoacetonitrile hydrochloride (25 g, 0.270 mol, Lancaster) in dichloromethane (1000 ml) was stirred in a 2 L Erlenmeyer flask under nitrogen at room temperature for 5 days. The reaction mixture was filtered to remove the precipitated ammonium chloride and the filtrate was evaporated to dryness in vacuo. The resulting residue was dissolved in ether (400 ml) washed with water (200 ml) and brine. After drying over magnesium sulfate the solution was evaporated to give (benzhydrylideneamino)-acetonitrile (47.89 g).

Step 2

A solution of sodium hydroxide (91 g, 2.275 mol) in water (91 ml) in a 2 L flask was cooled on ice under nitrogen and then treated with benzyl triethyl ammonium chloride (2.0 g, 0.0088 mol, Aldrich) and (benzhydrylideneamino)acetonitrile (47.89 g) in toluene (100 ml). 1,2-Dibromoethane (23 ml, 122.4 mmol, Aldrich) was then added dropwise over 25 min, to the reaction mixture with mechanical stirring and cooling to maintain the internal temperature near +10° C. The reaction mixture was then stirred vigorously for 24 h at room temperature and then poured into ice water and extracted with toluene. The combined extracts were washed with brine and then treated with MgSO4 and Norite. After filtering, toluene was removed by rotary evaporation to give an oil (67 g). The residue was dissolved in boiling hexane (400 ml), treated with Norite and filtered hot and allowed to cool. A dark oil separated and which was removed by pipet (~2 ml). Scratching induced crystallization in the remaining solution which was cooled on ice for 2 h. Light yellow crystals were collected by filtration and washed with cold hexane to give 1-(benzhydrylideneamino)cyclopropanecarbonitrile (30.56 g).

Step 3

A mixture of 1-(benzhydrylideneamino)cyclopropanecarbonitrile (30.56 g, 0.124 mol) in concentrated HCl (12 ml) in water (100 ml) and ether (100 ml) was stirred at room temperature for 15 h. The ether layer was discarded and the aqueous layer was washed with ether. The aqueous layer was then freeze dried to give the title compound as a tan powder (13.51 g).

Reference I

Synthesis of 2(R)-amino-3-[2-(difluoromethoxy)phenylmethanesulfanyl]propionic acid

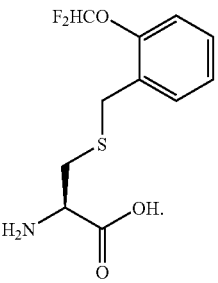

A solution of L-cysteine (5.1 g, 42.2 mmol) in 2N NaOH (42.2 ml) was cooled in an ice water bath. Neat 1-bromomethyl-2-difluoromethoxybenzene (10 g, 42.2 mmol) was added and the reaction mixture was allowed to stir and warm to room temperature over 4 h. The reaction mixture was cooled in an ice bath and the pH was adjusted 6 using 3N HCl, then 1N HCl when the white precipitate that formed became too thick to allow stirring. The precipitates were collected by vacuum filtration, washed with hexanes and dried by lyophilization to give the title compound (11.14 g) as a white solid.

Reference J

Synthesis of 4-amino-1-(2,2,2-trifluoroethyl)piperidine-4-carbonitrile hydrochloride

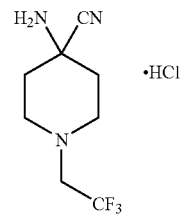

Step 1

In a solution of 1,4-dioxa-8-aza-spiro[4.5]decane (14.3 g, 100 mmol) in CH$_2$Cl$_2$ (200 ml) was added Et$_3$N (15.2 g, 150 mmol), DMAP (30 mg) and trifluoroacetic acid anhydride (25.2 g, 150 mmol) at 0° C., then allowed to warm-up to room temperature and stirred for 12 h. The reaction mixture was quenched with water and washed with 1N HCl and brine, dried with MgSO$_4$. Removal of the solvent, yielded 1-(1,4-dioxa-8-aza-spiro[4.5]dec-8-yl)-2,2,2-trifluoroethanone (35 g). The crude product was used in the next reaction.

Step 2

In the solution of 1-(1,4-dioxa-8-aza-spiro[4.5]dec-8-yl)-2,2,2-trifluoroethanone (20 g, 83.7 mmol) in THF, borane-methyl sulfide complex (83.7 ml, 2M solution in THF) was added at 0° C. After refluxing the reaction mixture for 12 h, the reaction was cooled and quenched with MeOH. After removal of THF, the residue was extracted with ethyl acetate and washed with brine, dried with MgSO₄ and concentrated to give 8-(2,2,2-trifluoroethyl)-1,4-dioxa-8-aza-spiro[4.5]decane (19 g) was obtained.

Step 3

8-(2,2,2-Trifluoroethyl)-1,4-dioxa-8-aza-spiro[4.5]decane (3.7 g, 16 mmol) was added to a solution of 5% HCl (45 ml) and acetone (8 ml). After refluxing for 12 h, the solvent was removed to give crude 1-(2,2,2-trifluoroethyl)piperidin-4-one hydrochloride which was used in the next reaction.

Step 4

A solution of ammonium chloride (3.2 g, 60 mmol) and potassium cyanide (2.94 g, 60 mmol) was prepared in water (25 ml) and 1-(2,2,2-trifluoroethyl)-piperidin-4-one hydrochloride (3.5 g, 15 mmol) was added and the reaction mixture was stirred for 2 days. The solution was then brought to pH 11 with sodium carbonate and the reaction mixture was extracted with ethyl acetate. After drying over Na₂SO₄, the solvent was removed to yield a mixture of 4-hydroxy-1-(2,2,2-trifluoroethyl)piperidine-4-carbonitrile and 4-amino-1-(2,2,2-trifluoroethyl)piperidine-4-carbonitrile. This mixture was then treated with 7N ammonia solution in MeOH for 12 h at room temperature. After removal of the solvent, the residue was dissolved in ethyl ether and treated with 4N HCl solution in dioxane. The solids were filtered and dried under vacuum, to yield 4-amino-1-(2,2,2-trifluoroethyl)piperidine-4-carbonitrile hydrochloride (2.5 g).

Example 1

Synthesis of N-(1-cyanocyclopropyl)-3-cyclopropylmethanesulfonyl-2(R)-[2,2-difluoro-2-(4-fluorophenoxy)-1(S)-(4-fluorophenyl)ethylamino]propionamide

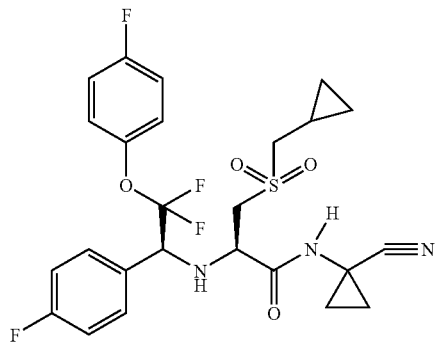

Step 1

A suspension of 60% of NaH in oil (3.84 g, 96 mmol) was washed three times with hexanes and the solid was suspended in dry DMF (80 ml). 4-Fluorophenol (8.96 g, 80 mmol) was slowly added over a period of 5 min and the reaction mixture was stirred at rt for about 10 min. The reaction mixture was cooled at 0° C. and 2-bromo-2,2-difluoroacetic acid ethyl ester (16.24 g, 80 mmol) was slowly added. The reaction mixture was heated at 90° C. for 20 h. After allowing the reaction to reach room temperature, ethyl ether (300 ml) was added and the suspension was washed with water and brine. After drying the organic layer over sodium sulfate for 15 min, the solvent was evaporated and the crude was purified by flash chromatography, using a mixture of ethyl acetate/hexanes (1/10) to give 2,2-difluoro-2-(4-fluorophenoxy)acetic acid ethyl ester as an oil (11.0 g, 59%).

Step 2

To a solution of 2,2-difluoro-2-(4-fluorophenoxy)acetic acid ethyl ester (2.9 g, 12 mmol) in a mixture of MeOH (20 ml) and THF (10 ml) was added a solution of NaOH (1.48 g, 37 mmol) in water (10 ml). The reaction mixture was stirred 20 h at rt and 1 h at 40° C. The reaction mixture was concentrated and the remaining aqueous solution was diluted with water (10 ml) and washed with hexanes. The solution was acidified to pH 3 by adding 1N HCl and the heterogeneous mixture was extracted with ethyl acetate. The combined extracts were washed with brine and after drying over sodium sulfate, the solvent was removed to obtain 2,2-difluoro-2-(4-fluorophenoxy)acetic acid as Step 3

To a solution of 2,2-difluoro-2-(4-fluorophenoxy)acetic acid (2.2 g, 10.6 mmol) in DCM (20 ml), were added oxalyl chloride (1.02 ml, 12 mmol) and a couple of drops of DMF and the reaction mixture was stirred for 2 h. The reaction mixture was evaporated to dryness and the yellowish residue was dissolved in DCM. The solvent was evaporated again and the residue was left under light vacuum (30 mm Hg) for 1 h. After dissolving the residue in DCM (20 ml), N,O-dimethyl hydroxylamine hydrochloride (1.24 g, 12.7 mmol) and TEA (25.4 mmol) were added. After stirring the reaction mixture overnight at rt, the heterogeneous mixture was washed with water and brine. After drying over sodium sulfate, the solvent was removed under vacuum to yield 2,2-difluoro-2-(4-fluorophenoxy)-N-methoxy-N-methylacetamide as an oil (2.05 g, 77%).

Step 4

To a solution of 2,2-difluoro-2-(4-fluorophenoxy)-N-methoxy-N-methylacetamide (2.03 g, 8.1 mmol) in anhydrous THF (15 ml) at 0° C., a solution of 1 M of lithium aluminum hydride in THF (4.05 ml, 4.05 mmol) was added. After stirring the solution for 3 h, 1N NaOH (2 ml) and ethyl ether (15 ml) were added. After 30 min, the reaction mixture was filtered through Celite and the cake was washed several times with ethyl ether. The organic phase was washed with brine and dried over sodium sulfate. The solvent was removed and the crude was purified using a short plug of silica gel to give 2,2-difluoro-2-(4-fluorophenoxy)-1-(N-methoxy-N-methylamino)ethanol as an oil (1.15 g, 57%).

Step 5

An ice water bath cooled solution of L-cysteine in 1N sodium hydroxide (740 ml) and dioxane (740 ml) was treated with bromomethylcyclopropane (50 g, 370 mmol). The reaction mixture was allowed to warm to room temperature and stirred for 16 h. Dioxane was removed under reduced pressure and the resulting aqueous solution was adjusted to pH 6 with 6N HCl and placed in a refrigerator for 20 h. The product was collected by vacuum filtration, washed with hexanes and lyophilized to give 2(R)-amino-3-cyclopropylmethylsulfanylpropionic acid (57.28 g) as a white solid.

Step 6

To an ice water cooled solution of lithium aluminum hydride (200 mM, 200 ml of 1.0 M) was added solid 2(R)-amino-3-cyclopropylmethylsulfanylpropionic acid. The addition was done by tapping in portions through a funnel in such a manner as to control hydrogen gas evolution. The ice bath was removed, and the reaction mixture was heated at reflux for 16 h. The reaction mixture was removed from heat and cooled in an ice water bath. Diethyl ether (110 ml) was added, followed by dropwise addition of water (5 ml), 15% aqueous sodium hydroxide (5 ml), and water (15 ml). After stirring in the ice water bath for 1.5 h, the reaction mixture was filtered. The filtrate was dried over anhydrous sodium sulfate, and concentrated to give 2(R)-amino-3-cyclopropylmethylsulfanylpropan-1-ol (14.9 g).

Step 7

A solution of 2(R)-amino-3-cyclopropylmethylsulfanylpropan-1-ol (14.9 g, 93 mmol), tert-butyldimethylchlorosilane (15.4 g, 102 mmol), 4-(N,N-dimethylamino)pyridine (182 mg, 1.49 mmol) and triethylamine (20.7 ml, 149 mmol) in dichloromethane (190 ml) was stirred at room temperature for 3.5 h. Saturated ammonium chloride (300 ml) was added and the layers were separated. The aqueous layer was extracted with dichloromethane and the combined organic layers were washed with brine, dried over anhydrous sodium sulfate, and concentrated to give 1-(tert-butyldimethylsilanyloxy)-2(R)-cyclopropylmethylsulfanylmethylethylamine (24.06 g).

Step 8

A solution of 1-(tert-butyldimethylsilanyloxy)-2(R)-cyclopropylmethylsulfanylmethyl-ethylamine (1.38 g, 5 mmol) and 2,2-difluoro-2-(4-fluorophenoxy)-1-(N-methoxy-N-methylamino)-ethanol (1.25 g, 5 mmol) in benzene was refluxed for 2 h in a Dean Stark apparatus. After evaporation of the solvent, the crude was purified by flash chromatography to give [2-(tert-butyldimethylsilanyloxy)-1(R)-(cyclopropylmethylsulfanylmethyl)ethyl]-[2,2-difluoro-2-(4-fluorophenoxy)ethylidene]amine as an oil (2.2 g, 100%).

Step 9

To a solution of 4-fluorobromobenzene (0.589 ml, 5.36 mmol) in anhydrous THF (5 ml) at −78° C., under nitrogen, a solution of 2.5 M of BuLi in hexanes (2.1 ml, 5.36 mmol) was added. After stirring the reaction mixture for 1 h at −78° C., a solution of [2-(tert-butyldimethylsilanyloxy)-1(R)-cyclopropylmethylsulfanylmethylethyl]-[2,2-difluoro-2-(4-fluorophenoxy)ethylidene]amine (0.8 g, 1.78 mmol) in THF (5 ml) was added. After stirring for 2 h at −40° C., the reaction mixture was diluted with ethyl ether and the solution was washed with 10% ammonium chloride solution, brine and dried over sodium sulfate. Concentration under vacuum followed by column chromatography over silica gel with ethyl acetate/hexanes (1/10) gave [2-(tert-butyldimethylsilanyloxy)-1(R)-cyclopropylmethylsulfanylmethylethyl]-[2,2-difluoro-2-(4-fluorophenoxy)-1(S)-(4-fluorophenyl)-ethyl]amine (0.75 g, 77%) as an oil.

Step 10

To a solution of [2-(tert-butyldimethylsilanyloxy)-1(R)-cyclopropylmethylsulfanylmethyl-ethyl]-[2,2-difluoro-2-(4-fluorophenoxy)-1(S)-(4-fluorophenyl)ethyl]amine (1.06 g, 1.94 mmol) in dry THF (10 ml) at 0° C., a 1M solution of tetrabutylammonium fluoride (2.3 ml, 2.3 mmol) was added. After stirring for 3 h at 0° C., the reaction mixture was diluted with ethyl ether (20 ml) and washed with sat. ammonium chloride solution (20 ml), brine (10 ml) and dried over sodium sulfate. After removal of the solvent under vacuum, the crude was purified by flash chromatography using ethyl acetate/hexanes (2/8) as eluent to give 3-cyclopropylmethylsulfanyl-2(R)-[2,2-difluoro-2-(4-fluorophenoxy)-1(S)-(4-fluorophenyl)ethylamino]propan-1-ol as an oil (0.418 g, 74%).

Step 11

To a heterogeneous mixture of 0.5 M of periodic acid in acetonitrile (30.2 ml, 15 mmol), 1 mg/ml solution of chromium oxide in acetonitrile (8 ml) and water (0.270 ml, 0.015 mol) at −5° C., a solution of 3-cyclopropylmethylsulfanyl-2 (R)-[2,2-difluoro-2-(4-fluorophenoxy)-1(S)-(4-fluorophenyl)ethylamino]propan-1-ol (0.65 g, 1.51 mmol) in acetonitrile (10 ml) was slowly added. After stirring the reaction mixture for 4 h at 0° C., 2-propanol (1 ml) was added and the stirring was continued for additional 30 min. After concentrating the reaction mixture to about half of its original volume, the residue was diluted with ethyl ether (50 ml) and washed with 5% solution of NaH$_2$PO$_4$ (20 ml), 0.5% solution of NaHSO$_3$ (10 ml) and brine. After drying over sodium sulfate, the solution was evaporated to dryness under vacuum to yield 3-cyclopropylmethanesulfonyl-2(R)-[2,2-difluoro-2-(4-fluorophenoxy)-1(S)-(4-fluorophenyl)ethylamino]propionic acid as a yellow solid (0.505 g, 70%).

Step 12

To a stirred mixture of 3-cyclopropylmethanesulfonyl-2 (R)-[2,2-difluoro-2-(4-fluoro-phenoxy)-1(S)-(4-fluorophenyl)ethylamino]propionic acid (0.2 g, 0.42 mmol) and 1-aminocyclopropanecarbonitrile hydrochloride (0.060 g, 0.5 mmol) in DMF (3 ml), HATU (0.16 g, 0.42 mmol) and diisopropylethylamine (0.183 ml, 1 mmol) was added. After stirring overnight at room temperature, the reaction mixture was diluted with ethyl acetate and washed with water, sat. NaHCO$_3$ and brine. After drying over sodium sulfate, the solvent was evaporated and the residue was purified by flash chromatography, using ethyl acetate/hexanes (1/1) as eluent to give the title compound as a white solid (0.09 g, 39%). $^1$HNMR (DMSO-d$_6$): δ 9.01 (1H, s), 7.47 (2H, m), 7.21 (2H, m), 7.13 (2H, m), 4.29 (1H, q), 3.74 (1H, m), 3.4 (2H, m), 3.19 (3H, m), 1.36 (2H, m), 1.10 (1H, m), 1.00 (1H, m), 0.72 (1H, m), 0.57 (2H, m), 0.30 (2H, m). LC/MS, M+1: 540.3; M−1: 538.3.

Example 2

Synthesis of N-(4-cyanotetrahydrothiopyran-4-yl)-3-cyclopropylmethanesulfonyl-2(R)-[2,2-difluoro-2-(4-fluorophenoxy)-1(S)-(4-fluorophenyl)ethylamino] propionamide

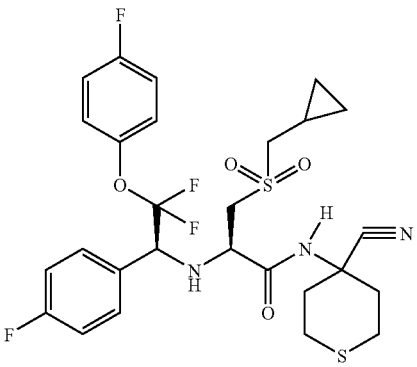

Following the procedure described in Example 1 above, but substituting 4-aminotetrahydrothiopyrane-4-carbonitrile for 1-aminocyclopropanecarbonitrile hydrochloride provided the title compound (28%). LC/MS, M+1: 600.7; M−1: 598.6.

Example 3

Synthesis of N-(4-cyano-1,1-dioxohexahydro-1λ⁶-thiopyran-4-yl)-3-cyclopropylmethanesulfonyl-2(R)-[2,2-difluoro-2-(4-fluorophenoxy)-1(S)-(4-fluorophenyl)ethylamino]-propionamide

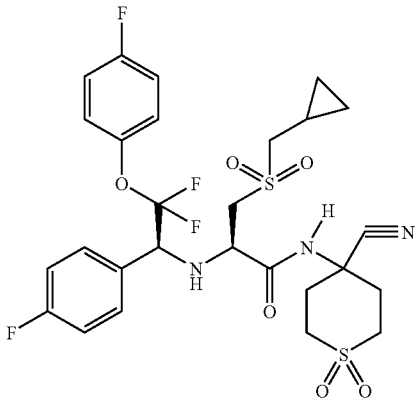

To a solution of N-(4-cyanotetrahydrothiopyran-4-yl)-3-cyclopropylmethanesulfonyl-2(R)-[2,2-difluoro-2-(4-fluorophenoxy)-1(S)-(4-fluorophenyl)ethylamino]propionamide (0.063 g, 0.1 mmol) in MeOH (10 ml) at 45° C., a solution of OXONE (0.3 mmol) in water (1 ml) was added. After stirring for 3 h at 45° C., the solvent was evaporated under vacuum and the residue was partitioned between DCM (15 ml) and water (15 ml). The organic phase was separated and the aqueous solution was extracted with DCM. The combined organic layers were washed with brine and dried over sodium sulfate. After removal of the solvent under vacuum, the crude was purified by preparative TLC, using ethyl acetate/hexanes (1/1) as mobile phase to give the title compound as a white solid (55%). ¹HNMR (DMSO-$d_6$): δ 8.82 (1H, s), 7.47 (2H, dd), 7.17 (6H, m), 4.32 (1H, q), 3.96 (1H, m), 3.40 (1H, m), 3.37 (4H, m), 3.00 (2H, m), 2.37 (2H), 1.15 (2H, m), 0.59 (3H, m), 0.30 (3H, m). LC/MS, M+1: 632.5; M−1: 630.6.

Example 4

Synthesis of N-(1-cyanocyclopropyl)-3-cyclopropylmethanesulfonyl-2(R)-[2,2-difluoro-2-(4-fluorophenylsulfanyl)-1(s)-(4-fluorophenyl)ethylamino]propionamide

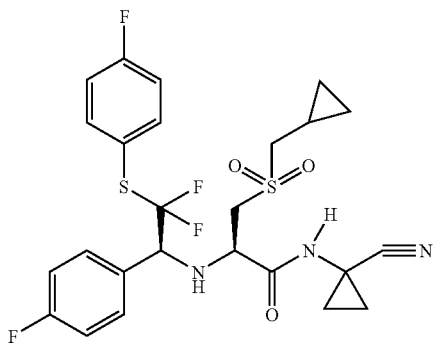

Proceeding as described in Example 1 above but substituting 4-fluorophenol with 4-fluoro-benzenethiol gave the title compound was obtained as an off-white solid (11%). ¹HNMR (DMSO-$d_6$): δ 8.97 (1H, s), 7.55 (2H, m), 7.41 (2H, m), 7.28 (2H, t), 7.20 (2H, t), 4.30 (1H, m), 3.70 (1H, m) 3.58 (1H, m), 3.41 (1H, m), 3.25 (3H, m), 1.33 (2H, m), 1.11 (1H, m), 0.94 (1H, m), 0.60 (3H, m), 0.37 (2H, m). LC/MS, M+1: 556.2; M−1: 554.5; and N-(1-cyanocyclopropyl)-3-cyclopropylmethanesulfonyl-2(R)-[2,2-difluoro-2-(4-fluorophenylsulfinyl)-1(S)-(4-fluorophenyl)ethylamino]propionamide as a by-product. ¹HNMR (DMSO-$d_6$): δ 8.92 (1H, s), 7.65 (2H, m), 7.41 (2H, m), 7.32 (2H, m), 7.10 (2H, m), 4.60 (1H, m), 3.67 (1H, m), 3.43 (1H, m), 3.25 (2H, m), 3.08 (2H, m), 1.18 (1H, m), 1.10 (1H, m), 1.00 (1H, m), 0.75 (1H, m), 0.54 (2H, m), 0.32 (2H, m), 0.05 (1H, m). LC/MS: M+1: 572.3; M−1: 570.3.

Example 5

Synthesis of N-(1-cyanocyclopropyl)-3-cyclopropylmethanesulfonyl-2(R)-[2,2-difluoro-2-(4-fluorophenylsulfonyl)-1(S)-(4-fluorophenyl)ethylamino]propionamide

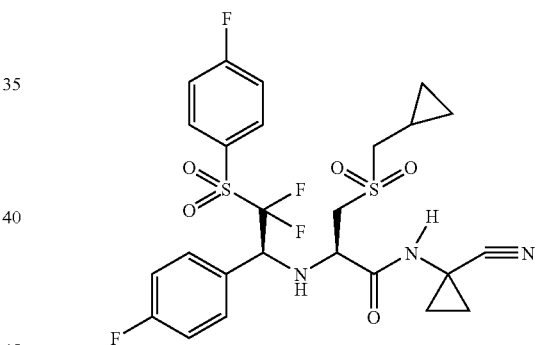

To a solution of N-(1-cyanocyclopropyl)-3-cyclopropylmethanesulfonyl-2(R)-[2,2-difluoro-2-(4-fluorophenylsulfanyl)-1(S)-(4-fluorophenyl)ethylamino]propionamide (0.108 g, 0.188 mmol), prepared as described in Example 4 above, in MeOH (10 ml), a solution of OXONE (0.233 g, 0.378 mmol) in water (1 ml) was added. After stirring the mixture for 4 H at 50° C., methanol was removed under vacuum and the aqueous residue was diluted with water (10 ml). The reaction mixture was extracted with DCM and the combined extracted was washed with brine (10 ml). After drying over sodium sulfate, the solvent was evaporated and the residue purified by flash chromatography, using a mixture ethyl acetate/hexanes (6/4) as eluent to give the title compound as a solid (22%). ¹HNMR (DMSO-$d_6$): δ 9.01 (1H, s), 7.97 (2H, m), 7.56 (2H, m), 7.41 (2H, m), 7.18 (2H, t), 4.73 (1H, m), 3.68 (1H, m), 3.39 (1H, m), 3.12 (4H, m), 1.29 (2H, m), 1.05 (1H, m), 0.91 (1H, m), 0.60 (2H, m), 0.39 (3H, m). LC/MS, M+1: 588.3; M−1: 586.3.

Example 6

Synthesis of N-(1-cyanocyclopropyl)-3-cyclopropyl-methanesulfonyl-2(R)-[2,2-difluoro-2-(4-fluorophenoxy)-1(s)-(3-methoxyphenyl)ethylamino]propionamide

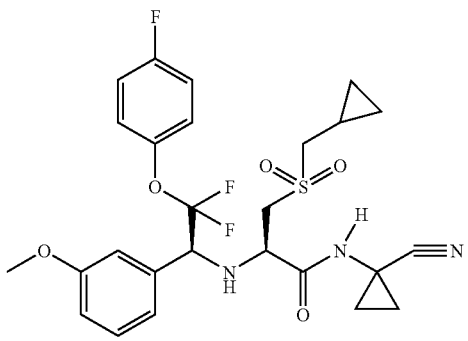

Proceeding as described in Example 1 above, but substituting 4-fluorobromobenzene with 3-methoxybromobenzene in Step 9 provided the title compound as a solid (30%). ¹HNMR (DMSO-d₆): δ 9.03 (1H, s), 7.24 (3H, m), 7.17 (2H, m), 6.95 (3H, m), 4.23 (1H, m), 3.76 (3H, s), 3.30 (5H, m), 1.37 (2H, m), 1.12 (1H, m), 0.97 (1H, m), 0.73 (1H, m), 0.58 (2H, d), 0.32 (2m, m). LC/MS, M+1: 552.4; M−1: 550.5.

Example 7

Synthesis of N-(1-cyanocyclopropyl)-3-cyclopropyl-methanesulfonyl-2(R)-[2,2-difluoro-2-(4-fluorophenoxy)-1(S)-(thiophen-3-yl)ethylamino]propionamide

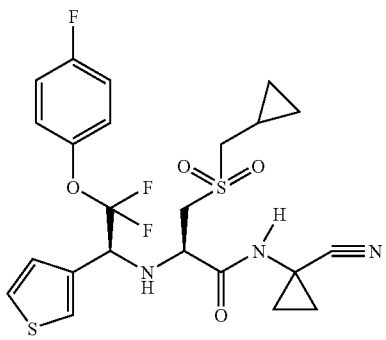

Proceeding as described in Example 1 above, but substituting 3-bromothiophene instead of 4-fluorobromobenzene in Step 9 provided the title compound. LC/MS, M+1: 528.4, M−1: 526.4.

Example 8

Synthesis of N-(1-cyanocyclopropyl)-3-cyclopropyl-methanesulfonyl-2(R)-[2,2-difluoro-2-(4-methylsulfonylophenoxy)-1(S)-(4-fluorophenyl)ethylamino]propionamide

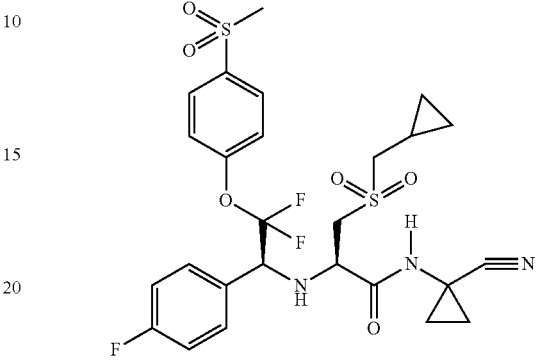

Step 1

Proceeding as described in Example 1, Step 1 above, but substituting 4-methylsulfanyl-phenol for 4-fluorophenol provided 2,2-difluoro-2-(4-methylsulfanylphenoxy)acetic acid ethyl ester as an oil.

Step 2

To a solution of 2,2-difluoro-2-(4-methylsulfanylphenoxy)acetic acid ethyl ester (19.8 g, 75 mmol) in dry ether (200 ml) at −70° C., a 1 M solution of DIBALH in hexanes (113 ml, 113 mmol) was added slowly. Ater stirring for 2 h at −70° C., methanol (4 ml) and water (27 ml) were dropwise added and the reaction mixture was left stirring at rt for 30 min. The heterogeneous mixture was filtered through a plug of Celite and the filtrate was diluted with ether (200 ml). The organic layer was washed with brine and dried over sodium sulfate. The solvent was evaporated to yield 2,2-difluoro-2-(4-methylsulfanylphenoxy)-acetaldehyde monohydrate which was then converted to the title compound as described in Example 1, Steps 8-12 above. Note: In step 11, both the sulfur atoms were oxidized to sulfonyl group. ¹HNMR (DMSO-d₆): δ 9.05 (1H, s), 7.99 (2H, m), 7.52 (2H, dd), 7.41 (2H, d), 7.25 (2H, t), 4.39 (1H, q), 3.80 (1H, m), 3.51 (2H, m), 3.36 (3H, s), 3.35 (2H, m), 3.20 (1H, m), 1.39 (2H, m), 1.13 (1H, m), 1.02 (1H, m), 0.75 (1H, m), 0.59 (2H, m), 0.31 (2H, m). LC/MS: M+1: 600.2; M−1: 598.2.

Example 9

Synthesis of N-(1-cyanocyclopropyl)-2(S)-[2,2-difluoro-2-pyridin-2-yl-1(S)-(4-fluorophenyl)ethylamino]pentamide

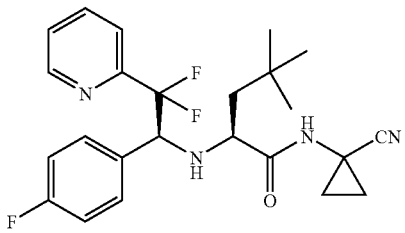

Step 1

(3-Methyloxetan-3-yl)methanol (20 g, 190 mmol) was added to a solution of toluene sulfonylchloride (54.3 g, 285 mmol) in dry pyridine (100 ml) and the reaction mixture was stirred at room temperature for 2 h. The reaction mixture was poured into crushed ice and stirred vigorously for 30 min. The precipitates were filtered and dried to give toluene-4-sulfonic acid 3-methyl-oxetan-3-ylmethyl ester (37 g) as a white powder.

Step 2

To a 1M solution of NaOH (135 ml, 135 mmol) was added 2(S)-amino-4,4-dimethylpentanoic acid (commercially available) (9.8 g, 67.5 mmol), followed by benzyloxycarbonyl chloride (11.6 ml, 80.99 mmol) in acetonitrile (20 ml) and the reaction mixture was stirred for 12 h at room temperature. The solvent was evaporated using rotavap and the slurry was washed with hexane and then adjusted the pH to 6 using 6N HCl. The resulting solution was extracted with ethyl acetate. The organic layer was washed with brine and dried over $MgSO_4$. The solvent was evaporated to get 2(S)-benzyloxycarbonylamino-4,4-dimethylpentanoic acid (18.6 g) as a sticky gum which was used in the next step without further purification.

Step 3

Toluene-4-sulfonic acid 3-methyloxetan-3-ylmethyl ester (18.6 g, 66 mmol) was added to a solution of cesium carbonate (13.04 g, 39 mmol) in water (15 ml) and stirred until the solution became clear. The solution was lyophilized overnight to give flaky white solid. The solid was dissolved in DMF (50 ml) and 2(S)-benzyloxycarbonylamino-4,4-dimethylpentanoic acid (15.99 g, 66 mmol) and sodium iodide (2 g, 13.2 mmol) were added. After 48 h, the solution was diluted with 500 ml of ethyl acetate, washed with water, saturated solution of sodium bicarbonate solution (50 ml) and brine. The ethyl acetate layer was separated and dried over $MgSO_4$. The solvent was evaporated and the crude was column chromatographed on a silica gel column using 20:80 EtOAc:Hexane as eluent to give 2(S)-benzyloxycarbonylamino-4,4-dimethylpentanoic acid 3-methyloxetan-3-ylmethyl ester (21.5 g) as a white solid.

Step 4

To a solution of 2(S)-benzyloxycarbonylamino-4,4-dimethylpentanoic acid 3-methyl-oxetan-3-ylmethyl ester (21.5 g, 59 mmol) in dry DCM (50 ml) was added $BF_3.Et_2O$ (0.4 ml, 3.2 mmol). After 5 h, triethylamine (0.9 ml, 6.4 mmol) was added and stirring was continued for 30 min at room temperature. The solvent was evaporated using a rotavap and the resulting oil was redissolved in ethyl acetate and was washed with 50 ml of 3% $NH_4Cl$ solution followed by brine. The ethyl acetate layer was dried over $MgSO_4$, the solvent was evaporated and the residue was purified with column chromatography using silica gel and 20:80 EtOAc:Hexane as eluent to give [3,3-dimethyl-1(S)-(4-methyl-2,6,7-trioxabicyclo[2.2.2]oct-1-yl)butyl]carbamic acid benzyl ester (15.5 g).

Step 5

[3,3-Dimethyl-1(S)-(4-methyl-2,6,7-trioxabicyclo[2.2.2] oct-1-yl)butyl]carbamic acid benzyl ester (15 g) was dissolved in ethyl acetate (300 ml) and after degassing with nitrogen, 10% Pd—C (1.5 g) was added under nitrogen atmosphere. The reaction mixture was hydrogenated at 50 psi for 4 h. The solution was filtered through celite and washed with EtOAc. The solvent was removed to give 3,3-dimethyl-1(S)-(4-methyl-2,6,7-trioxabicyclo[2.2.2]oct-1-yl)butylamine (8 g) as a white solid.

Step 6

2-Bromopyridine (4.5 g, 28.5 mmol) and 2-bromo-2,2-difluoroacetic acid ethyl ester (6 g, 29.6 mmol) were dissolved in DMF (25 ml) and Cu (4.5 g, 71.2 mmol) was added. The reaction mixture was heated at 50° C. for 18 h and after adding isopropyl acetate (30 ml) the reaction mixture was quenched with a solution of potassium dihydrogen phosphate (8 g) in water (50 ml). The resultant solution was stirred for 30 min, filtered and washed with isopropyl acetate. The organic layer was separated, washed with water and brine. After drying the organic layer was dried over $MgSO_4$, it was filtered and concentrated to give 2,2-difluoro-2-pyridin-2-ylacetic acid ethyl ester (4.3 g) as a brown liquid.

Step 7

DIBAL-H (2 ml) was added to a solution of 2,2-difluoro-2-pyridin-2-ylacetic acid ethyl ester (400 mg, 2 mmol) in dry ether (2.5 ml) at −78° C. After 4 h, methanol (0.5 ml) and water (2 ml) were added. The reaction mixture was warmed to room temperature and the emulsion formed was filtered through celite and washed with ether. The organic layer was separated, washed with brine and dried over $MgSO_4$. The solvent was evaporated to get a thick liquid. To the crude liquid was added DCM (1 ml) and hexane (3 ml) and left overnight in cold. The precipitated solid was filtered and washed with hexane to give 2,2-difluoro-2-pyridin-2-ylacetaldehyde (150 mg) as a white solid. 2,2-Difluoro-2-pyridin-2-ylacetaldehyde was reacted with 3,3-dimethyl-1(S)-(4-methyl-2,6,7-trioxabicyclo[2.2.2]oct-1-yl)butylamine as described in Example 1, Step 8 above to give (2,2-difluoro-2-pyridin-2-ylethylidene)-[3,3-dimethyl-1(S)-(4-methyl-2, 6,7-trioxabicyclo[2.2.2]oct-1-yl)butyl]amine (600 mg) as a thick liquid.

Step 8

1-Bromo-4-fluorobenzene (1.12 g, 6.4 mmol) of was dissolved in ether (20 ml) and cooled to −78° C. nBuLi (2.56 ml, 2.5M, 6.4 mmol) was added and the reaction mixture was stirred for 1 h. (2,2-Difluoro-2-pyridin-2-ylethylidene)-[3,3-dimethyl-1(S)-(4-methyl-2,6,7-trioxabicyclo[2.2.2]oct-1-yl) butyl]amine (1.18 g, 3.2 mmol) was added and stirring was continued for 2 h while the solution was allowed to warm up to 40° C. Water (5 ml) was added and the reaction mixture was allowed to warm to room temperature. The organic layer was separated, washed with brine and was dried over $MgSO_4$. The solvent was evaporated and the crude was purified by flash column chromatography using silica gel and 20:80 ethylacetate:hexane as an eluent to give [2,2-difluoro-1(S)-(4-fluorophenyl)-2-pyridin-2-ylethyl]-[3,3-dimethyl-1(S)-(4-methyl-2,6,7-trioxabicyclo[2.2.2]oct-1-yl)butyl]amine (265 mg).

Step 9

To a solution of [2,2-difluoro-1(S)-(4-fluorophenyl)-2-pyridin-2-ylethyl]-[3,3-dimethyl-1(S)-(4-methyl-2,6,7-trioxabicyclo[2.2.2]oct-1-yl)butyl]amine (265 mg, 0.571 mmol) in a mixture of THF (5 ml) and water (5 ml) was added 1N HCl (2 ml, 2 mmol) and the reaction mixture was stirred at room temperature for 2 h. 1N NaOH (3.6 ml, 3.6 mmol) was added and stirring was continued at room temperature for 4 h. The solvent was evaporated using rotavap and 6N HCl was added dropwise to adjust the pH to 6. The precipitates were filtered and dried to obtain 2(S)-[2,2-difluoro-1(S)-(4-fluorophenyl)-2-pyridin-2-ylethylamino]-4,4-dimethylpentanoic acid (100 mg) as a white solid which was converted to the title compound as described in Example 1, Step 12 above. LC/MS: 443.2 $(M-1)^{-1}$, 445.4 $(M+1)^{+1}$, 466.9 (M+Na). $^1$HNMR (DMSO-$d_6$): δ 8.7 (d, 1H), 8.6 (s, 1H), 7.95 (t, 1H), 7.6 (d, 1H), 7.55 (t, 1H), 7.4 (d, 2H), 7.2 (d, 2H), 4.6 (m, 1H), 2.6 (t, 1H), 1.3 (m, 4H), 0.6 (S, 10H), 0.25 (t, 1H).

Example 10

Synthesis of N-(1-cyanocyclopropyl)-2(S)-[2,2-difluoro-2-pyridin-2-yl-1(S)-(thiophen-3-yl)ethylamino]pentamide

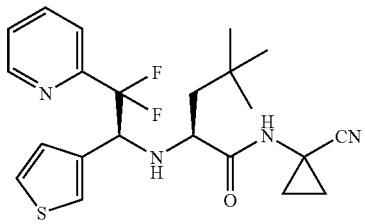

To a solution of 3-bromothiophene (597 mg, 6.3 mmol) in dry ether (10 ml) at −70° C. was added nBuLi (1.6 M, 2.5 ml) and the reaction mixture was stirred for 2 h at the same temperature. A solution of (2,2-difluoro-2-pyridin-2-ylethylidene)-[3,3-dimethyl-1(S)-(4-methyl-2,6,7-trioxabicyclo[2.2.2]oct-1-yl)butyl]amine (1.16 g, 3.15 mmol) (prepared as described in Example 9 above) in ether (5 ml) was added and stirring was continued while the reaction mixture was allowed to warm to −40° C. The reaction mixture was quenched with water and the organic layer was separated, washed with brine and dried over MgSO$_4$. The crude product was purified by column chromatographed to give (2,2-difluoro-2-pyridin-2yl-1(S)-thiophen-3-ylethyl)-[3,3-dimethyl-1(S)-(4-methyl-2,6,7-trioxa-bicyclo[2.2.2]oct-1-yl)butyl]amine (350 mg) which was converted to 2(S)-[2,2-difluoro-1(S)-(thiophen-3-yl)-2-pyridin-2-ylethylamino]-4,4-dimethylpentanoic acid as described in Example 9, Step 9 above and then converted to the title compound as described in Example 1, Step 12 above.

LC/MS: 431.2 (M−1)$^{−1}$, 433.0 (M+1)$^{+1}$, 455.2 (M+Na)$^+$.
$^1$HNMR (DMSO-d$_6$): δ 8.7 (d, 1H), 8.6 (s, 1H), 7.95 (t, 1H), 7.6 (d, 1H), 7.55 (t, 1H), 7.45 (d, 1H), 7.38 (d, 1H), 7.05 (d, 1H), 4.7 (m, 1H), 2.9 (t, 1H), 2.4 (m, 1H), 1.3 (m, 4H), 0.6 (S, 10H), 0.25 (t, 1H).

Example 11

Synthesis of N-(1-cyanocyclopropyl)-3-cyclopropylmethanesulfonyl-2(R)-[2,2-difluoro-2-(4-fluorophenyl)-1(S)-(4-fluorophenyl)ethylamino]propionamide

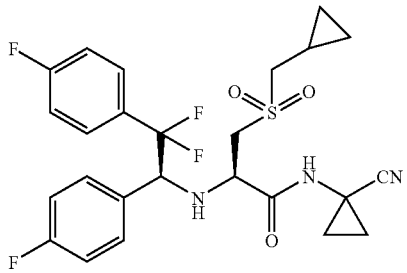

Step 1
1-Fluoro-4-iodobenzene (30 g, 135 mmol) and 2-bromo2,2-difluoroacetic acid ethyl ester (29 g, 142.9 mmol) were dissolved in DMF (100 ml) and Cu (21.5 g, 71.2 mmol) was added. The reaction mixture was heated at 90° C. for 18 h. Ethyl acetate (100 ml) was added and the reaction mixture was quenched with a solution of potassium dihydrogen phosphate (20 g) in water (200 ml). The resultant solution was stirred for 30 min, filtered and was washed with ethyl acetate. The organic layer was separated, washed with water and brine. The organic layer was dried over MgSO$_4$, filtered, and concentrated to give 2,2-difluoro-2-(4-fluorophenyl)acetic acid ethyl ester (26.5 g) as a yellow liquid.
Step 2
2,2-Difluoro-2-(4-fluorophenyl)acetic acid ethyl ester was converted to 2,2-difluoro-2-(4-fluorophenyl)acetaldehyde (7 g) by following the procedure described in Example 9, Step 7 above and then converted to the title compound by following Example 1, Steps 8-12 above.

LC/MS: 522.4 (M−1)$^{−1}$, 524.2 (M+1)$^{+1}$, 546.3 (M+Na)$^+$.
$^1$H NMR (CDCl$_3$): δ 7.7 (s, 1H), 7.2 (dd, 2H), 7.1 (dd, 2H), 7.0 (dd, 4H), 4.3 (m, 1H), 3.6 (d, 1H), 3.5 (m, 2H), 3.0 (d, 2H), 1.5 (d, 2H), 1 (m, 3H), 0.7 (m, 2H), 0.4 (m, 2H).

Example 12

Synthesis of N-(4-cyano-1,1-dioxo-hexahydro-1λ$^6$-thiopyran-4-yl)-3-cyclopropylmethanesulfonyl-2(R)-[2,2-difluoro-2-(4-fluorophenyl)-1(S)-(4-fluorophenyl)ethylamino]propionamide

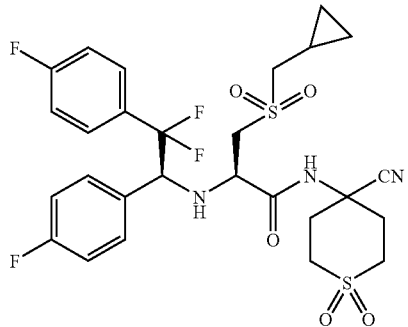

Step 1
To a solution of 3-cyclopropylmethanesulfonyl-2(R)-[2,2-difluoro-2-(4-fluorophenyl)-1(S)-(4-fluorophenyl)ethylamino]propionic acid (170 mg, 0.37 mmol) (prepared as described in Example 11 above, in DMF (2 ml) was added HATU (169 mg, 0.44 mmol), 4-aminotetrahydrothiopyran-4-carbonitrile (64.5 mg, 0.37 mmol) and diisopropylethylamine (258 μl) and the reaction mixture was stirred for 2 h at room temperature. The reaction mixture was diluted with ethyl acetate and washed with water, saturated solution of NaHCO$_3$ and brine. The organic layer was dried over MgSO$_4$ and evaporated to give N-(4-tetrahydrothiopyran-4-yl)-3-cyclopropylmethanesulfonyl-2(R)-[2,2-difluoro-2-(4-fluorophenyl)-1(S)-(4-fluorophenyl)ethylamino]propionamide (150 mg) which was used in the next step without further purification.
Step 2
To a solution of N-(4-tetrahydrothiopyran-4-yl)-3-cyclopropylmethanesulfonyl-2(R)-[2,2-difluoro-2-(4-fluorophenyl)-1(S)-(4-fluorophenyl)ethylamino]propionamide in methanol (5 ml) was added a solution of OXONE (268.66 mg) in water (1.5 ml) and the reaction mixture was heated at 50° C. for 2 h. The solvent was evaporated using rotavap and the residue was taken in ethyl acetate washed with water and brine. The organic layer was dried over MgSO₄ and the solvent was evaporated using the rotavap. The resulting crude was purified by preparative TLC using 50:50 hexane:ether as elutent to give title compound (50 mg) as a white solid.

LC/MS: 614.5 (M−1)$^{−1}$, 616.3 (M+1)$^{+1}$, 638.3 (M+Na)$^+$.
$^1$H NMR (CDCl₃): δ 7.8 (s, 1H), 7.2 (dd, 2H), 7.1 (dd, 2H), 7.0 (dd, 4H), 4.2 (m, 1H), 3.8 (d, 1H), 3.6 (d, 1H), 3.5 (m, 2H), 3.3 (m, 2H), 3.05 (d, 2H), 3.0 (d, 2H), 2.8 (m, 2H), 2.4 (m, 2H), 1.05 (m, 1H), 0.8 (m, 2H), 0.4 (m, 2H).

Example 13

Synthesis of N-(1-cyanocyclopropyl)-3-cyclopropyl-methanesulfonyl-2(R)-[2,2-difluoro-2-pyridin-3-yloxy-1(S)-(4-fluorophenyl)ethylamino]propionamide

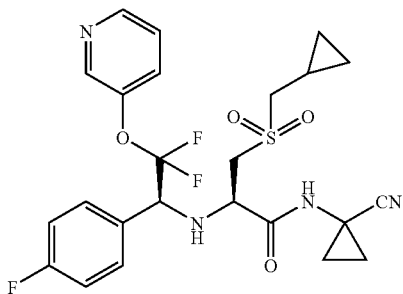

Step 1

A suspension of 60% of NaH in oil (2.52 g, 126 mmol) was washed three times with hexanes and the solid was suspended in dry DMF (100 ml). Pyridine-3-ol (10 g, 105 mmol) was slowly added over a period of 5 min and the reaction mixture was stirred at room temperature for about 10 min. The reaction mixture was cooled at 0° C. and 2-bromo-2,2-difluoro-acetic acid ethyl ester (21.32 g, 105 mmol) was slowly added. The reaction mixture was heated at 90° C. for 20 h. After cooling the reaction to reach room temperature, ethyl ether was added and the suspension was washed with water and brine. The organic layer was dried over sodium sulfate for 15 min, the solvent was evaporated and the crude was purified by flash chromatography, using 100% methylene chloride to obtain 2,2-difluoro-2-(pyridin-3-yloxy)acetic acid ethyl ester as a brown oil (8 g). 2,2-Difluoro-2-(pyridin-3-yloxy)acetic acid ethyl ester was converted to 2,2-difluoro-2-(pyridin-3-yloxy)acetaldehyde (7 g) by following the procedure described in Example 9, Step 7 above and then converted to the title compound by following Example 1, Steps 8-12 above.

LC/MS: 521.2 (M−1)$^{−1}$, 523.1 (M+1)$^{+1}$, 545.2 (M+Na)$^+$.
$^1$HNMR (cdcl₃): δ 8.5 (δ, 2H), 7.7 (s, 1H), 7.6 (s, 1H), 7.5 (d, 2H), 7.3 (d, 1H), 7.1 (dd, 2H), 4.3 (m, 1H), 3.6 (d, 1H), 3.5 (m, 2H), 3.0 (d, 2H), 1.5 (d, 2H), 1 (m, 3H), 0.7 (m, 2H), 0.4 (m, 2H).

Example 14

Synthesis of N-(1-cyanocyclopropyl)-3-cyclopropyl-methanesulfonyl-2(R)-[2,2-difluoro-2-(2-methylpyridin-5-yloxy-1(S)-(4-fluorophenyl)ethylamino]propionamide

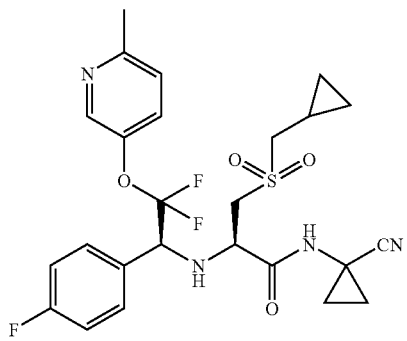

2,2-Difluoro-(6-methylpyridin-3-yloxy)acetaldehyde was prepared as described in Example 13, Step 1 and Example 9, Step 7 above and then converted to the title compound by proceeding as described in Example 1, Steps 8-12 above.
LC/MS: 535.0 (M−1)$^{−1}$, 537.1 (M+1)$^{+1}$, 559.1 (M+Na)$^+$.

Example 15

Synthesis of N-(1-cyanocyclopropyl)-3-cyclopropyl-methanesulfonyl-2(R)-[2,2-difluoro-2-(4-methylsulfonylophenoxy)-1(S)-(4-fluorophenyl)ethylamino]propionamide

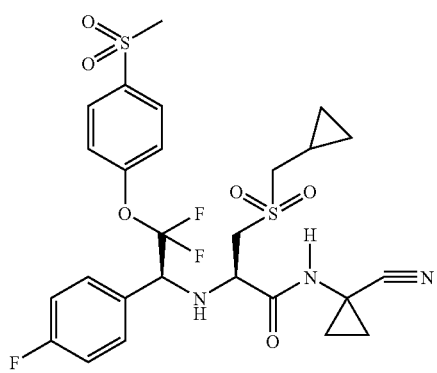

Step 1

To a solution of 4-fluorobromobenzene (2.9 ml, 26 mmol) in ethyl ether (15 ml) at −70° C., a 2.5M solution of n-BuLi in hexanes (10.4 ml, 26 mmol) was slowly added under nitrogen. After stirring for 1 h at −70° C., the reaction mixture was transferred slowly via a canula to a solution of 2,2-difluoro-2-(4-methylthiophenoxy)acetic acid ethyl ester (3.41 g, 13 mmol) (see Example 8) in ethyl ether at −70° C. After stirring for 3 h, the reaction mixture was diluted with ethyl ether (50 ml) and quenched by adding 10% solution of NH₄Cl. The aqueous phase was further extracted with ethyl ether. The combined organic layers were washed with brine and dried over sodium sulfate. The crude was purified by flash chromatography by using a mixture of EA/H (0.5/9.5) as eluent to give 2,2-difluoro-1-(4-fluorophenyl)-2-(4-methylsulfanylphenoxy)ethanone (2.76 g, 67%) as an oil.

Step 2

To a solution of 2,2-difluoro-1-(4-fluorophenyl)-2-(4-methylsulfanylphenoxy)ethanone (2.76 g, 8.84 mmol) and S-methyl-CS-oxazaborolidine in a mixture of DCM/Toluene (1/1, 40 ml) under nitrogen, at −70° C., a solution of catecholborane (1.27 g, 10.6 mmol) in DCM (2 ml) was slowly added. After stirring at −70° C. for 18 h, the reaction mixture was quenched by adding 4M solution of HCl in dioxane (3 ml). The heterogeneous mixture was stirred for 15 min at −70° C., then warmed to room temperature. Solvent was removed on a rotary evaporator and the resulting solution was diluted with hexanes (80 ml). Water (0.5 ml) was added and the mixture was stirred for 15 min. The solids were filtered and the filter cake was washed with hexanes. The filtrate was washed with 10% aqueous sodium metabisulfite (15 ml) and brine (15 ml). The organic phase was dried over sodium sulfate and the crude purified by flash chromatography, using EA/H (1/10) as eluent to give 2,2-difluoro-1(R)-(4-fluorophenyl)-2-(4-methylsulfanylphenoxy)ethanol (1.55 g, 56%) as a white solid.

Step 3

NaH (60% in oil, 1.54 g, 4.9 mmol) was washed several times with pentane, under nitrogen and then suspended in anhydrous ethyl ether (10 m) and cooled at 0° C. A solution of 2,2-difluoro-1(R)-(4-fluorophenyl)-2-(4-methylsulfanylphenoxy)ethanol in ethyl ether (10 ml) was added. After stirring the reaction mixture for 15 min, trifluoromethylsulfonyl chloride was added and the resulting mixture was stirred for 2 h at 0° C. The reaction mixture was diluted with hexanes (20 ml) and washed with saturated solution of NaHCO₃ and brine. After drying over magnesium sulfate, the solution was concentrated to give trifluoromethanesulfonic acid 2,2-difluoro-1(R)-(4-fluorophenyl)-2-(4-methylsulfanylphenoxy)ethyl ester (1.70 g, 77%) as an oil.

Step 4

A mixture of trifluoromethanesulfonic acid 2,2-difluoro-1(R)-(4-fluorophenyl)-2-(4-methylsulfanylphenoxy)ethyl ester (1.70 g, 3.8 mmol), 2(R)-amino-3-tritylsulfanylpropionic acid (1.38 g, 38 mmol) and diisiopropylethylamine (2.65 ml, 15.2 mol) in DCM (35 ml) was stirred for 19 h at room temperature. The solvent was evaporated under vacuum and the residue dissolved in ethyl ether (20 ml). The solution was washed with 1N HCl solution and brine. After drying over sodium sulfate, the solvent was evaporated and the crude was purified by flash chromatography, using a mixture of EA/H (1/3) as eluent to give 2(R)-[2,2-difluoro-1(S)-(4-fluorophenyl)-2-(4-methylsulfanylphenoxy)ethylamino]-3-tritylsulfanylpropionic acid (0.693 g, 27%) as a foam.

Step 5

To a solution of 2(R)-[2,2-difluoro-1(S)-(4-fluorophenyl)-2-(4-methylsulfanylphenoxy)-ethylamino]-3-tritylsulfanylpropionic acid (0.69 g, 1.04 mmol) in DCM (0.8 ml), TFA (0.322 ml, 4.18 mmol) and triethylsilane (0.332 ml) were added. After stirring 3 h, solvent and excess of TFA were evaporated under vacuum. The residue was dissolved in benzene and evaporated again on rotary evaporator to give 2(R)-[2,2-difluoro-1(S)-(4-fluorophenyl)-2-(4-methylsulfanyl-phenoxy)ethylamino]-3-mercaptopropionic acid. The residue was dissolved in 1N NaOH (4 ml) and the solution was used immediately in the next step.

Step 6

To the aqueous solution of 2(R)-[2,2-difluoro-1(S)-(4-fluorophenyl)-2-(4-methylsulfanyl-phenoxy)ethylamino]-3-mercaptopropionic acid (~1 mmol), tris(2-carboxyethyl)-phosphine hydrochloride (0.029 g, 0.1 mol) and (bromomethyl)cyclopropane (0.136 g, 1 mmol) were added. After stirring for 16 h, the solution was acidified to pH 2-3 by adding 1N HCl and the mixture was extracted with ethyl ether. The combined extracts were washed with brine and dried over sodium sulfate to give 3-cyclopropylmethanesulfanyl-2(R)-[2,2-difluoro-1(S)-(4-fluorophenyl)-2-(4-methylsulfanylphenoxy)ethylamino]propionic acid (0.460 g, 95%) as a foam which was converted to N-(1-cyanocyclopropyl)-3-cyclopropylmethylsulfanyl-2(R)-[2,2-difluoro-1(S)-(4-fluorophenyl)-2-(4-methylsulfanylphenoxy)ethylamino]-propionamide as described in Example 1, Step 12 above.

Step 7

To a solution of 3-cyclopropylmethanesulfanyl-2(R)-[2,2-difluoro-1(S)-(4-fluorophenyl)-2-(4-methylsulfanylphenoxy)ethylamino]propionic acid (0.270, 0.504 mmol) in N-methylpyrrolidone (5 ml), an aqueous solution of OXONE (0.929 g, 1.51 mmol, in 5 ml of water) was added at room temperature. After stirring the heterogeneous mixture for 5 h, water was added (30 ml). The flask was cooled at 0° C. and the reaction mixture stirred for 20 min. The solid was collected by filtration and washed with plenty of cold water. The white solid was left in drying pistol at 50° C., overnight. The crude material (0.235 g) was dissolved in ethyl acetate and hexane was added until cloudiness was observed. After stirring for 1 h, the white solid was filtered and washed with pentane to give the title compound (0.189 g, 62%). ¹HNMR (dmso-d6): δ 9.05 (1H, s), 7.99 (2H, m), 7.52 (2H, dd), 7.41 (2H, d), 7.25 (2H, t), 4.39 (1H, q), 3.80 (1H, m), 3.51 (2H, m), 3.36 (3H, s), 3.35 (2H, m), 3.20 (1H, m), 1.39 (2H, m), 1.13 (1H, m), 1.02 (1H, m), 0.75 (1H, m), 0.59 (2H, m), 0.31 (2H, m). LC/MS: M+1: 600.2; M−1: 598.2.

BIOLOGICAL EXAMPLES

Example 1

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5-10 seconds on a shaker plate, covered and incubated for 30 min at room temperature. Z-FR-AMC (20 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5-10 seconds on a shaker plate, covered and incubated for 30 min at room temperature. Z-Phe-Arg-AMC (4 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5-10 seconds on a shaker plate, covered and incubated for 30 min at room temperature. Z-Phe-Arg-AMC (1 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); P-mercaptoethanol, 2.5 mM; and BSA, 0.00%. Human cathepsin S (0.05 pMoles in 25 μL of assay buffer) was added to the dilutions. The assay solutions were mixed for 5-10 seconds on a shaker plate, covered and incubated for 30 min at room temperature. Z-Val-Val-Arg-AMC (4 nMoles in 25 μL of assay buffer containing 10% DMSO) was added to the assay solutions and hydrolysis was followed spectrophotometrically (at λ 460 nm) for 5 min. Apparent inhibition constants ($K_i$) were calculated from the enzyme progress curves using standard mathematical models.

Compounds of the invention were tested by the above-described assay and observed to exhibit cathepsin S inhibitory activity.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5-10 seconds on a shaker plate, covered and incubated for 30 min at room temperature. Z-Phe-Arg-AMC (2 nMoles in 25 μL of assay buffer containing 10% DMSO) was added to the assay solutions and hydrolysis was followed spectrophotometrically (at λ 460 μm) for 5 min. Apparent inhibition constants ($K_i$) were calculated from the enzyme progress curves using standard mathematical models.

Compounds of the invention were tested by the above-described assay and observed to exhibit cathepsin F inhibitory activity.

Example 1

Representative Pharmaceutical Formulations Containing a Compound of Formula (I)

Oral Formulation

| | |
|---|---|
| Compound of Formula (I) | 10-100 mg |
| Citric Acid Monohydrate | 105 mg |
| Sodium Hydroxide | 18 mg |
| Flavoring | |
| Water | q.s. to 100 ml |

Intravenous Formulation

| | |
|---|---|
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 ml |

Tablet Formulation

| | |
|---|---|
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

I claim:
1. A compound of Formula (I):

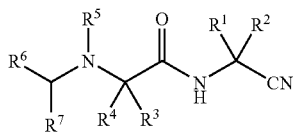

wherein:
$R^1$ and $R^2$ taken together with the carbon atom to which both $R^1$ and $R^2$ are attached form (i) cycloalkylene optionally substituted with one or two $R^b$ independently selected from alkyl or halo or (ii) heterocyclylalkylene optionally substituted with one to four $R^c$ independently selected from alkyl or halo or optionally substituted with one to three $R^c$ where two $R^c$ are independently selected from alkyl, halo, haloalkyl, or hydroxyl and the third $R^c$ is hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, $-S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl;
$R^3$ is hydrogen;
$R^4$ is cycloalkylalkyl, aralkyl, heteroaralkyl, heterocyclylalkyl, or -alkylene-$X^1$—$R^{22}$ [wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CONR^{24}$—, or —$NR^{23}SO_2NR^{24}$— (where each $R^{23}$ and $R^{24}$ are independently hydrogen, alkyl, or acyl and n3 is 0-2) and $R^{22}$ is hydrogen, alkyl, haloalkyl, cycloalkyl, cycloalkylalkyl, aryl, aralkyl, heteroaryl, heteroaralkyl, heterocyclyl, or heterocyclylalkyl] wherein said alkylene chain in -alkylene-$X^1$—$R^{22}$ is optionally substituted with one to six halo and the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl; or
$R^3$ and $R^4$ together with the carbon atom to which they are attached form cycloalkylene;
$R^5$ is hydrogen;
$R^6$ is -haloalkylene-$X^2$—$R^{25}$ [wherein $X^2$ is —O— or $SO_{n4}$— where n4 is 0-2 and $R^{25}$ is alkyl, haloalkyl, cycloalkyl, cycloalkylalkyl, heterocyclyl, heterocyclylalkyl, aryl, aralkyl, heteroaryl, or heteroaralkyl] wherein the aromatic or alicyclic ring in $R^{25}$ is optionally substituted by one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl; and $R^7$ is alkyl, haloalkyl, aryl, heteroaryl, cycloalkyl, or heterocyclyl attached to the carbon atom substituted with the $R^7$ group via a carbon-carbon single bond; wherein the aromatic or alicyclic ring in $R^7$ is optionally substituted with one, two, or three $R^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl and further wherein the aromatic or alicyclic ring in $R^g$ is optionally substituted with one, two, or three $R^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl; or
a pharmaceutically acceptable salt thereof.

2. The compound of claim 1 where $R^1$ and $R^2$ together with the carbon atom to which they are attached form cycloalkylene.

3. The compound of claim 1 where $R^1$ and $R^2$ together with the carbon atom to which they are attached form cyclopropylene.

4. The compound of claim 1 wherein $R^3$ and $R^5$ are hydrogen and $R^4$ is -alkylene-$S(O)_{n3}$—$R^{22}$ where n3 is 0-2 and $R^{22}$ is alkyl, cycloalkylalkyl, aryl, aralkyl, heteroaryl, or heteroaralkyl wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl.

5. The compound of claim 1 wherein $R^6$ is —$CF_2$—$X^2$—$R^{25}$ where $X^2$ is —O— or —$S(O)_{n4}$— where n4 is 0-2 and $R^{25}$ is aryl or heteroaryl optionally substituted with one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl.

6. The compound of claim 1 wherein $R^6$ is —$CF_2$—$X^2$—$R^{25}$ where $X^2$ is —O— and $R^{25}$ is phenyl or heteroaryl optionally substituted with one or two $R^e$ independently selected from alkyl, halo, hydroxy, alkoxy, alkoxyalkyl, haloalkoxy, cyano, nitro, carboxy, alkoxycarbonyl, alkylsulfonyl, or aminosulfonyl.

7. The compound of claim 1 wherein $R^6$ is —$CF_2$—$X^2$—$R^{25}$ where $X^2$ is a single bond and $R^{25}$ is aryl or heteroaryl optionally substituted with one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl.

8. The compound of claim 4 wherein $R^7$ is alkyl.

9. The compound of claim 4 wherein $R^7$ is haloalkyl.

10. The compound of claim 4 wherein $R^7$ is phenyl optionally substituted with one, two, or three $R^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl wherein the aromatic or alicyclic ring in $R^g$ is optionally substituted with one, two, or three $R^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl.

11. The compound of claim 4 wherein $R^7$ is phenyl optionally substituted with one, two, or three $R^e$ independently selected from alkyl, halo, haloalkyl, haloalkoxy, alkoxy, or alkylsulfonyl.

12. The compound of claim 4 wherein $R^7$ is heteroaryl optionally substituted with one, two, or three $R^g$ independently selected from alkyl, halo, haloalkyl, hydroxy, alkoxy, haloalkoxy, alkylsulfonyl, carboxy, alkoxycarbonyl, aminosulfonyl, hydroxyalkyl, aminocarbonyl, aminoalkyl, alkoxyalkyl, cyano, aryl, aralkyl, heteroaryl, heteroaralkyl, heterocyclyl, or heterocyclylalkyl wherein the aromatic or alicyclic ring in $R^g$ is optionally substituted with one, two, or three $R^h$ independently selected from alkyl, halo, haloalkyl, alkoxy, cycloalkyl, monosubstituted amino, disubstituted amino, aminocarbonyl, acyl, carboxy, alkoxycarbonyl, alkylthio, alkylsulfonyl, aminosulfonyl, arylsulfonyl, heteroaryl, heteroarylsulfonyl, heterocyclyl, heterocyclylsulfonyl, hydroxyalkyl, or alkoxyalkyl.

13. The compound of claim 4 wherein $R^7$ is pyridinyl, thiophenyl, furanyl, or pyrrolyl optionally substituted with one or two $R^e$ independently selected from alkyl, halo, haloalkyl, haloalkoxy, alkoxy, or alkylsulfonyl.

14. The compound of claim 1 wherein:
$R^1$ and $R^2$ together with the carbon atom to which they are attached form cycloalkylene or heterocycloalkylene;
$R^6$ is $-CF_2-X^2-R^{25}$ where $X^2$ is $-O-$, $-S-$, or $-SO_2-$ and $R^{25}$ is aryl or heteroaryl optionally substituted with one, two, or three $R^e$ independently selected from alkyl, halo, hydroxy, hydroxyalkyl, alkoxy, alkoxyalkyl, haloalkyl, haloalkoxy, cyano, nitro, acyl, aryl, aryloxy, arylsulfonyl, heteroaryl, heteroaryloxy, heteroarylsulfonyl, heterocyclyl, heterocyclyloxy, cycloalkyl, cycloalkyloxy, carboxy, alkoxycarbonyl, alkylsulfonyl, aminosulfonyl, or aminoalkyl;
$R^3$ and $R^5$ are hydrogen;
$R^7$ is phenyl or heteroaryl optionally substituted with one, two, or three $R^g$ independently selected from alkyl, halo, haloalkyl, hydroxy, alkoxy, haloalkoxy, alkylsulfonyl, carboxy, alkoxycarbonyl, aminosulfonyl, hydroxyalkyl, or aminocarbonyl.

15. The compound of claim 14 wherein $R^4$ is -alkylene-S$(O)_{n3}-R^{22}$ where n3 is 0-2 and $R^{22}$ is alkyl, cycloalkylalkyl, aryl, aralkyl, heteroaryl, or heteroaralkyl wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl.

16. The compound of claim 15 wherein $R^4$ is phenylmethanesulfonylmethyl, 4-tert-butylphenylmethanesulfonylmethyl, 2-fluorophenylmethanesulfonylmethyl, 3-fluorophenylmethanesulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenyl-methanesulfonylmethyl, 2-trifluoromethylphenylmethane-sulfonylmethyl, 3-trifluoromethylphenylmethanesulfonylmethyl, 4-trifluoromethylphenyl-methanesulfonylmethyl, 2-cyanophenylmethanesulfonylmethyl, 3-cyanophenylmethane-sulfonylmethyl, 2-bromophenylmethanesulfonylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-difluoromethoxyphenylmethanesulfonylmethyl, 3-difluoromethoxyphenylmethanesulfonylmethyl, 4-difluoromethoxyphenylmethanesulfonylmethyl, 3-chloro-2-fluorophenylmethane-sulfonylmethyl, 3,5-dimethylphenylmethanesulfonylmethyl, 3,5-bis-trifluoromethylphenyl-methanesulfonylmethyl, 2,5-difluorophenylmethanesulfonylmethyl, 2,6-difluorophenylmethanesulfonylmethyl, 2,3-difluorophenylmethane-sulfonylmethyl, 3,4-difluorophenylmethanesulfonylmethyl, 2,4-difluorophenylmethanesulfonylmethyl, 2,5-difluorophenylmethanesulfonylmethyl, 3,4-dichlorophenylmethanesulfonylmethyl, 2,6-dichlorophenylmethanesulfonylmethyl, 2-fluoro-3-methylphenylmethanesulfonyl-methyl, 4-fluoro-2-trifluoromethoxyphenylmethanesulfonylmethyl, 2-fluoro-6-trifluoromethylphenylmethanesulfonylmethyl, 2-fluoro-3-trifluoromethylphenyl-methanesulfonylmethyl, 2-fluoro-4-trifluoromethylphenylmethanesulfonylmethyl, 2-fluoro-5-trifluoromethyl-phenylmethanesulfonylmethyl, 4-fluoro-3-trifluoromethyl-phenylmethanesulfonylmethyl, 2-chloro-5-trifluoromethylphenylmethane-sulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonylmethyl, 3,4,5-trifluorophenylmethanesulfonyl-methyl, trimethoxyphenylmethanesulfonylmethyl, pyridin-2-ylmethanesulfonylmethyl, pyridin-3-ylmethanesulfonylmethyl, pyridin-4-ylmethanesulfonylmethyl, N-oxypyridin-2-ylmethanesulfonylmethyl, 2-trifluoropyridin-6-ylmethanesulfonylmethyl, pyrazin-2-ylmethanesulfonylmethyl, cyclohexylmethanesulfonylmethyl, cyclohexylmethane-sulfonylmethyl, cyclopropylmethanesulfonylmethyl, thiophene-2-sulfonylmethyl, 5-chlorothien-2-ylmethane-sulfonylmethyl, or 3,5-dimethyl-isoxazol-4-ylmethanesulfonylmethyl.

17. The compound of claim 15 wherein $R^4$ is cyclopropylmethanesulfonylmethyl, 2-difluoromethoxyphenylmethanesulfonylmethyl, or phenylmethanesulfonylmethyl.

18. A pharmaceutical composition comprising a compound of claim 1 or a pharmaceutically acceptable salt thereof, in admixture with one or more suitable excipients.

19. A method for treating a disease in an animal selected from asthma, arthritis, atherosclerosis, COPD, MS, and psoriasis, which method comprises administering to the animal a pharmaceutical composition comprising a compound of claim 1 or a pharmaceutically acceptable salt thereof, in admixture with one or more suitable excipients.

20. The compound of claim 1, having the following formula:

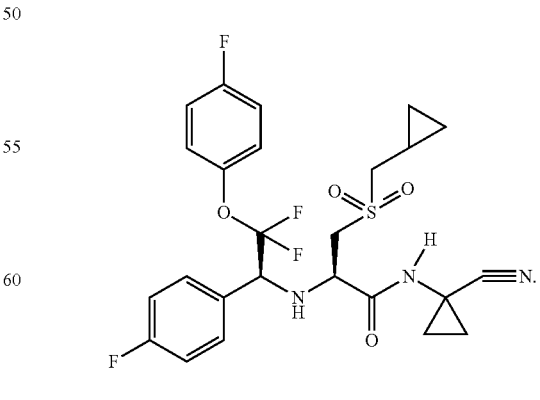

* * * * *